United States Patent
Jarvius

(10) Patent No.: US 10,227,632 B2
(45) Date of Patent: Mar. 12, 2019

(54) ROLLING CIRCLE AMPLIFICATION METHOD

(71) Applicant: Q-LINEA AB, Uppsala (SE)

(72) Inventor: Jonas Jarvius, Uppsala (SE)

(73) Assignee: Q-Linea AB, Uppsala (SE)

(*) Notice: Subject to any disclaimer, the term of this patent is extended or adjusted under 35 U.S.C. 154(b) by 323 days.

(21) Appl. No.: 15/037,022

(22) PCT Filed: Nov. 28, 2014

(86) PCT No.: PCT/EP2014/076005
§ 371 (c)(1),
(2) Date: May 16, 2016

(87) PCT Pub. No.: WO2015/079042
PCT Pub. Date: Jun. 4, 2015

(65) Prior Publication Data
US 2016/0257991 A1    Sep. 8, 2016

(30) Foreign Application Priority Data
Nov. 29, 2013  (GB) .................................. 1321123.0

(51) Int. Cl.
| | | |
|---|---|---|
| *C12Q 1/68* | (2018.01) | |
| *C12Q 1/6806* | (2018.01) | |
| *C12Q 1/6844* | (2018.01) | |
| *C12Q 1/682* | (2018.01) | |
| *C12Q 1/6853* | (2018.01) | |

(52) U.S. Cl.
CPC ........... *C12Q 1/6806* (2013.01); *C12Q 1/682* (2013.01); *C12Q 1/6844* (2013.01); *C12Q 1/6853* (2013.01); *C12Q 2531/125* (2013.01)

(58) Field of Classification Search
CPC ............... C12Q 1/6806; C12Q 1/6853; C12Q 2525/131; C12Q 2531/125
See application file for complete search history.

(56) References Cited

U.S. PATENT DOCUMENTS

| | | | |
|---|---|---|---|
| 5,514,546 A | 5/1996 | Kool | |
| 5,714,320 A | 2/1998 | Kool | |
| 5,854,033 A | 12/1998 | Lizardi | |
| 6,077,668 A | 6/2000 | Kool | |
| 6,096,880 A | 8/2000 | Kool | |
| 6,143,495 A | 11/2000 | Lizardi et al. | |
| 6,183,960 B1 | 2/2001 | Lizardi | |
| 6,274,320 B1 | 8/2001 | Rothberg et al. | |
| 6,368,802 B1 | 4/2002 | Kool | |
| 6,558,928 B1 | 5/2003 | Landegren | |
| 6,576,448 B2 | 6/2003 | Weissman et al. | |
| 6,867,028 B2 | 3/2005 | Janulaitis et al. | |
| 7,033,753 B1 | 4/2006 | Kool | |
| 7,074,564 B2 | 7/2006 | Landegren | |
| 7,135,312 B2 | 11/2006 | Kool | |
| 7,320,860 B2 | 1/2008 | Landegren et al. | |
| 7,790,388 B2 | 9/2010 | Landegren et al. | |
| 7,883,849 B1 | 2/2011 | Dahl | |
| 7,906,490 B2 | 3/2011 | Kool | |
| 7,989,166 B2 | 8/2011 | Koch et al. | |
| 8,053,188 B2 | 11/2011 | Gullberg et al. | |
| 8,080,393 B2 | 12/2011 | Koch et al. | |
| 8,518,640 B2 | 8/2013 | Drmanac et al. | |
| 2005/0287526 A1* | 12/2005 | Landegren ........... C12Q 1/6848 435/6.12 |
| 2010/0028953 A1* | 2/2010 | Koch ..................... C12N 15/10 435/91.1 |
| 2013/0224729 A1 | 8/2013 | Church et al. | |

FOREIGN PATENT DOCUMENTS

| | | |
|---|---|---|
| GB | 2 378 245 A | 2/2003 |
| WO | WO 92/01813 A1 | 2/1992 |
| WO | WO 99/49079 A1 | 9/1999 |
| WO | WO 01/40516 A2 | 6/2001 |
| WO | WO 01/61037 A1 | 8/2001 |
| WO | WO 03/012119 A2 | 2/2003 |
| WO | WO 03/091406 A2 | 11/2003 |
| WO | WO 2005/070630 A1 | 8/2005 |
| WO | WO 2005/111236 A1 | 11/2005 |
| WO | WO 2006/108423 A2 | 10/2006 |
| WO | WO 2013/119888 A1 | 8/2013 |

OTHER PUBLICATIONS

Dahl et al., 'Circle-to-circle amplification for precise and sensitive DNA analysis', (2004) Proceedings of the National Academy of Sciences, National Academy of Sciences, US 101(13): 4548-4553.
Dean et al., 'Rapid amplification of plasmid and phage DNA using Phi29 DNA polymerase and multiply-primed rolling circle amplification', (2001) Genome Research 11: 1095-1099.
Drmanac et al, 'Human genome sequencing using unchained base reads on self-assembling DNA nanoarrays', (2010) Science 1 327(5961): 78-81.
Ericsson et al, 'A dual-tag microarray platform for high-performance nucleic acid and protein analyses', (2008) Nucleic Acids Research, vol. 36, No. 8, e45: 1-9.
Göransson et al., 'A single molecule array for digital targeted molecular analyses', (2009) Nucleic Acids Res. 37(1):e7: 1-9.
Göransson et al., 'Rapid identification of bio-molecules applied for detection of biosecurity agents using rolling circle amplification', (2012) PLOS ONE 7(2): e31068: 1-9.

(Continued)

*Primary Examiner* — David C Thomas
(74) *Attorney, Agent, or Firm* — Fay Sharpe LLP

(57) ABSTRACT

A method for performing a rolling circle amplification (RCA) reaction includes at least two rounds of RCA. The method includes providing a concatemeric first RCA product having a multiplicity of monomer repeats, each repeat representing a complementary copy of a first RCA template, wherein the nucleic acid molecule to be detected and/or analyzed, or its compliment, is contained in the first RCA template. The first RCA product is cleaved into monomer units which are reduced in size compared to the monomer repeat of the first RCA template. Monomer units resulting from the cleavage are circularized to form second RCA templates, which are smaller than the first RCA template. A second RCA reaction is performed on the second RCA template and a primer for the second RCA to form a second RCA product. The second RCA product, or a monomer unit derived from it, is detected or analyzed.

Figure 1:
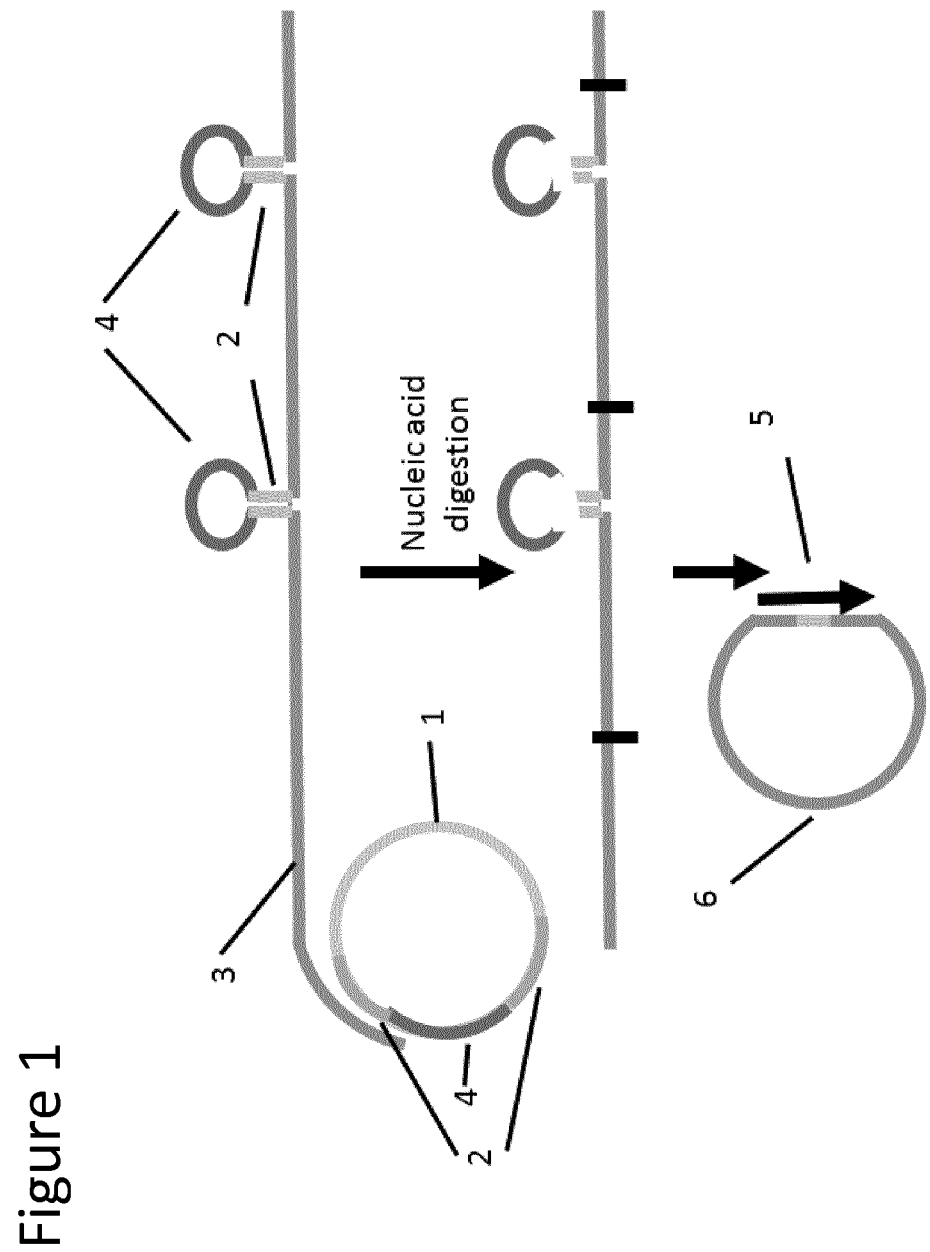

34 Claims, 4 Drawing Sheets
Specification includes a Sequence Listing.

(56) References Cited

OTHER PUBLICATIONS

Gu and Breaker, 'Production of single-stranded DNAs by self-cleavage of rolling-circle amplification products', (2013) Biotechniques 54: 337-343.
Hardenbol et al., 'Multiplexed genotyping with sequence-tagged molecular inversion probes', (2003) Nature Biotechnology 21: 673-678.
Jarvius et al., 'Digital quantification using amplified single-molecule detection', (2006) Nature Methods, vol. 3, No. 9: 725-727 (and Supplementary Note/Supplementary Methods/Supplementary Figures/Supplementary Table—16 pages).
Jarvius, J. (2006), 'DNA Tools and Microfluidic Systems for Molecular Analysis', Acta Universitatis Upsaliensis. Digital Comprehensive Summaries of Uppsala Dissertations from the Faculty of Medicine 161. 65 pp.
Porreca et al, 'Multiplex amplification of large sets of human exons', (2007) Nature Methods 4(11): 931-937.
Russell et al., 'Gold nanowire based electrical DNA detection using rolling circle amplification', (2014) ACS Nano, 2014, 8 (2), pp. 1147-1153.
Smith et al., 'Detection of nucleic acid targets using ramified rolling circle DNA amplification: a single nucleotide polymorphism assay model', (2013) PLOS ONE 7(8): e65053: 1-8.
Wählby et al., 'Sequential immunofluorescence staining and image analysis for detection of large numbers of antigens in individual cell nuclei' (2002) Cytometry, 47(1):32-41.
International Search Report of International Application No. PCT/EP2014/076005 dated May 15, 2015, 6 pages.
Written Opinion of International Application No. PCT/EP2014/076005 dated May 15, 2015, 7 pages.

* cited by examiner

ROLLING CIRCLE AMPLIFICATION METHOD

The present invention lies generally in the field of nucleic acid amplification by rolling circle amplification (RCA), and relates particularly to an improved method of "circle to circle" amplification (C2CA).

Rolling circle replication (RCR) is a mechanism used in nature for the replication of circular DNA molecules such as plasmids or viruses The reaction has been adopted as the basis for a laboratory method for amplifying circular molecules and, as well as having utility in methods of amplifying or producing nucleic acids, has been demonstrated to be useful in a variety of assays which use or generate a circular nucleic acid molecule as a reporter; in such assay methods the circular molecule is amplified (replicated) by RCA and the replicated or amplified circular nucleic acid molecule is detected. In other methods, desired, or target molecules may be circularised and amplified by RCA. Accordingly, rolling circle replication (RCR) is now commonly referred to as rolling circle amplification (RCA), and these terms are used interchangeably herein.

RCA relates to the synthesis of nucleic acid molecules using a circular single stranded nucleic acid molecule, e.g. an oligonucleotide, as rolling circle template and a strand-displacing polymerase to extend a primer which is hybridised to the circular template(the strand displacing activity displaces the primer and effectively causes the circle to "roll"). The primer may in certain typical assays be provided by a target nucleic acid (RNA or DNA) molecule. The addition of a polymerase and nucleotides starts the synthesis reaction, i.e. polymerisation. As the rolling circle template is endless, the resultant product is a long single stranded nucleic acid molecule composed of tandem repeats, or monomers, that are complementary to the rolling circle template (i.e. a concatemer).

Circles (circular templates) for RCA reactions may be formed or provided in various ways, for example they may be provided as reporter molecules, formed from probes which are circularised as part of a detection reaction (e.g. padlock probes the ends of which are directly or indirectly ligated upon hybridisation to a target molecule to form a circularised molecule), target molecules for isolation or detection may be circularised, or substrates for amplification may be circularised or incorporated into circular nucleic acid molecules, for example by ligating or hybridising adaptors for circularisation to the ends of the target or substrate molecules.

The concatemeric RCA product may be detected in homogenous ("in solution") or heterogeneous (solid phase-based) assays. For instance, a RCA reaction may result in a 1000-fold amplification of the circle in just 1 hour (based on a circle consisting of about 100 nucleotides). Thus, the RCA of a circular oligonucleotide may result in a RCA product that forms a bundle or "blob" of DNA that can be about 1 μm in diameter. The product, i.e. blob, may be visualised, for example detected by labelling, e.g. by the hybridisation of nucleic acid probes conjugated to fluorescent (or other) labels which allows the blob to be visualised by (fluorescence) microscopy or flow cytometry. In other embodiments, the RCA products may be reduced to monomers by digestion with a restriction enzyme or a ribozyme, which are then detected. The RCA product or monomers derived therefrom may be detected and/or analysed by sequencing or other sequence analysis procedures.

Due to the ability of the RCA reaction to generate a readily detectable signal it is useful as a reporter system for detection of any nucleic acid molecule in a sample, which may be a target nucleic acid molecule (i.e. a nucleic acid molecule to be detected, or where the nucleic acid molecule is the "analyte" of the assay), or it may be a nucleic acid molecule which is to be detected as a marker (or proxy) for the presence of the target analyte. RCA has also been utilised in methods for the detection of other analytes, i.e. analytes other than nucleic acid molecules such as proteins, peptides etc. In this respect, a variety of assays have been developed in which a nucleic acid molecule may be used to directly or indirectly tag or label a target analyte in a sample and detection of the nucleic acid molecule serves to indicate the presence of the analyte in the sample. In some methods a new nucleic acid molecule may be generated in a sample (i.e. a nucleic acid molecule that was not present in the original sample and was not one of the components added to the sample) when one or more molecules that interact with, e.g. bind to, the target analyte. The detection of the generated nucleic acid molecule is indicative of the analyte in a sample.

Various methods based upon detecting such a proxy or marker nucleic acid molecule using an RCA reaction as part of the detection strategy are well described in the art, including for example, immuno-RCA, assays using padlock probes and proximity probe assays which generate a circular nucleic acid molecule. In all these cases, the methods rely on providing or generating a circular nucleic acid molecule which may then be used as a substrate (template) for a RCA reaction, and the RCA product may then be detected as a substitute for detecting the target analyte directly.

For example a proximity assay is described by Landegren et al. in WO 99/49079. In such a method the ends of the added linear oligonucleotide(s) are brought into juxtaposition for ligation to form a circular template for RCA by hybridising to one or more circularisation templates provided by the nucleic acid domain of one or more proximity probes. Various such assay formats are described in WO 01/61037.

It will accordingly be evident that RCA may be of utility in the specific detection of any nucleic acid molecule in a sample, regardless of whether it is the "original" target analyte in a sample or it is a "proxy" target analyte generated by the interaction of specific detection molecules, e.g. proximity probes, with the target analyte, e.g. protein. RCA may also be useful in the detection of amplified nucleic acid molecules. For instance, in samples in which the target nucleic acid molecule is present in low amounts, e.g. rare transcripts, RCA can be used to "enhance" detection by increasing the amount of nucleic acid that is available to be detected.

RCA has proved to be particularly useful for parallel amplification of many nucleic acid molecules simultaneously, and to generate un-skewed amplification of multiple sequences i.e. it is particularly useful in multiplex contexts (see for example, WO 03/012119, WO 99/49079 and WO 2005/111236).

RCA is however a linear process and accordingly is slow compared to exponential amplification methods. In order to increase the amount or rate of amplification various modifications of the basic RCA reaction have been proposed, including to provide a more than linear amplification, for example to improve sensitivity in assays based upon detecting an RCA product. Thus for example hyperbranched RCA (HBRCA/HRCA) has been developed (U.S. Pat. Nos. 6,183,960 and 6,143,495). HBRCA may however result in an uncontrolled and variable amount of amplified product being produced and may be prone to false starts. Furthermore double-stranded product is produced in this reaction and it may in many cases be desirable to have a single-stranded nucleic acid molecule, e.g. for downstream detection.

In WO 03/012199 a method, termed the circle-to-circle amplification (C2CA) method, based on repeat RCA reactions, is described, which may be used for amplifying the product generated from a first RCA reaction. In this method the first generation RCA product (generated from a first "circle" or circular RCA template) is cleaved into monomers (for example each monomer corresponding to one tandem repeat in the concatemeric product), which are circularised and then used as RCA templates (i.e. as second circles or circular templates) in a further round of RCA. Cleavage may be achieved by hybridising an oligonucleotide to a sequence (restriction site sequence) present in each repeat (monomer) of the RCA product to create a double-stranded restriction cleavage or recognition site and cleaving with a restriction enzyme to cleave the product into monomers.

Despite these developments, there is a need for improvements in methods of RCA and in particular for increasing amplification efficiency, for example the speed of amplification. More particularly it would be beneficial to increase the speed or rate at which amplification product may be generated in C2CA reactions, which may find particular application in detection assays, for example in in vitro diagnostic or detection methods, e.g. methods for the detection of pathogens, or microorganisms or viruses more generally, in clinical or environmental samples, or for detecting other analytes or target molecules. The present invention is directed towards such an aim.

The invention is based on the concept of improving the efficiency of the C2CA reaction by speeding up the "second" or successive RCA reaction. This is achieved by reducing the size of the "second" RCA template—in the method of the invention only a part (or parts) of each monomer repeat of the first RCA product are selected and used for circularisation, so that the next, successive ("second") RCA reaction is performed using a shorter circular RCA template than the first generation RCA which produced the first RCA product (RCP). Since the rate of RCP production depends on the size of the circle (circular RCA template), the shorter the circle, the more RCP can be produced in a given unit or amount of time. Thus rather than cleaving the first RCP to generate monomers which correspond to the tandem repeats (monomer repeats) of the RCP, or which (if they are cleaved within monomer repeats rather than between them), correspond in size to the monomer repeats, as in traditional or conventional C2CA methods, or indeed in any other C2CA methods reported to date, the present invention is based on cleaving the first RCP in such a way that parts of the monomer repeat sequences may be removed, or the monomer repeats may be cleaved into two or more parts, and one or more of the parts or reduced-length monomer sequences thereby generated are circularised to generate the templates for the second or successive RCA reaction.

Product generation (i.e. amplification) may be increased even further by a possible third or further generations of RCA, wherein in each successive round the monomerisation reaction (cleavage) is designed to reduce the size of the monomer unit released or generated by the cleavage.

Thus, by selecting part of the first RCA product that is transformed into a new set of circles it is possible to shorten the sequence of the second or further RCA template, improving the efficiency of amplification by allowing more monomers to be produced per minute of amplification. Various means of selecting part of the first RCA product are possible, as described below. By decreasing the size of the amplification circle from e.g. 90 nucleotides in the first round to e.g. 45 nucleotides in the second round it is possible to increase the amount of monomeric DNA to be produced after two rounds of subsequent C2CA by four fold, and 8-fold if there are three subsequent rounds of amplification after the first RCA step. Put another way, it is sufficient to perform two rounds of 10 minutes each compared to two rounds of 20 minutes each if the original length of the sequence had been preserved and thus obtain the same result in half the time. If both of the generated 45-mer fragments from the monomeric unit of the first RCA product in the example above are transformed into new circles, the number of monomers per minute is increased four-fold after only one round of RCA, compared to if the whole monomeric unit would have been used, such as is the case of traditional C2CA as described in WO 03/012199.

Accordingly in a first aspect, the present invention provides a method for performing a rolling circle amplification (RCA) reaction comprising at least two rounds of RCA, said method comprising:
(a) providing a concatemeric first RCA product comprising a multiplicity of monomer repeats, each repeat representing a complementary copy of a first RCA template (a "first" RCA template "circle");
(b) cleaving the first RCA product into monomer units, wherein the monomer unit is reduced in size as compared to the monomer repeat of the first RCA product;
(c) circularising monomer units resulting from said cleavage to form second RCA templates ("second circles"), wherein the second RCA template is smaller than the first RCA template;
(d) performing a second RCA reaction using said second RCA template of (c) and a primer for said second RCA, to form a second RCA product;
wherein any one or more of steps (a) to (d) may be performed sequentially or in combination.

Thus steps (a), (b), (c) and (d) may be performed sequentially or substantially simultaneously (i.e. as part of the same reaction, in the sense that that reagents for the various steps are added or are present together, although it will be recognised of course that monomerisation/cleavage needs to occur before the generated monomer units are circularised by ligation). In particular, steps (b) and (c) may occur in combination.

The first RCA product of step (a) contains multiple repeat (or tandem) copies (or monomer repeats) of a sequence, each repeat being a complementary copy of the circular RCA template used to produce the first RCA product (the "first RCA template"), i.e. it is a concatemer of monomers. Thus the same cleavage sites, or recognition sites for cleavage enzymes, may be repeated in each monomer repeat, allowing for cleavage to result in a multiplicity of cleaved monomer units. Each monomer repeat of the first RCA product thus contains one or more (e.g. two or more than two) cleavage sites or cleavage recognition sites, for example recognition sites for a cleavage enzyme, which may allow a cleavage site to be generated, for example, or which may be the recognition site for an enzyme with a separate cleavage site. As will be described in more detail below, cleavage may result in the release or generation of more than one monomer unit per cleavage reaction (e.g. per monomer) and each of these, or only a selected monomer unit may subsequently be circularised in step (c). As used herein the term "multiple" or "multiplicity" means two or more, e.g. at least 2, 3, 4, 5, 6, 10, 20, 30, 50, 70 or 100 or more.

The cleavage step (b) is thus a step of monomerisation, cleaving the first RCA product into a multiplicity of monomer units. Each monomer unit need not correspond to, or derive from, a single monomer repeat of the first RCA product; depending on the mode of cleavage, or location of the cleavage sites, which may be located within monomer repeats and not necessarily at the junctions between them, the released monomer may contain sequences derived from more than one monomer repeat. Thus for example a cleaved monomer unit may comprise sequences derived from two adjacent monomer repeats. However, because there is a multiplicity of identical monomer repeats each comprising identical cleavage sites, cleavage results in a multiplicity of identical monomer units. In many embodiments of the invention, cleavage is performed in such a way that a monomer unit is released or generated which is reduced in size as compared to the monomer repeat In other words the step of cleaving the first RCA product may result in the generation of monomer units which are smaller (shorter) than the monomer repeat. However, it is also possible, as will be described in more detail below, to carry out separate monomerisation and size reduction steps. Thus there may be a separate step of cleaving the first RCA product into monomers (or monomer units) and then further cleaving the monomer units to reduce their size, i.e. to cleave off or remove a portion (or part or sequence) of the monomer unit. Accordingly, cleavage of the first RCA product may occur simultaneously with reducing the size of the monomer unit or there may be a separate step of reducing the size of the monomer unit.

The released monomer units (or reduced monomer units) are circularisable, and may be used to generate circular RCA templates for a subsequent further ("second") RCA reaction. As will be will described in more detail below, modes of cleavage may be selected which result in the formation or release of different monomer units (i.e. more than one type of monomer unit), and some or all of these may be circularised. In other words it may be selected which released monomer units are circularised.

By "circularisable" it is meant that the monomer unit is formed or released as a linear molecule having ligatable ends which may circularised by ligating the ends together directly or indirectly, i.e. to each other, or to the respective ends of an intervening ("gap") oligonucleotide or to an extended 3' end of the monomer unit. The monomer unit is circularised prior to the second or further RCA by ligation, which may be self-templated by the monomer unit itself, or templated by an added (i.e. external) ligation template, namely an oligonucleotide which serves as a ligation template for circularisation of monomer units. Since different monomer units may be generated by cleavage it may be selected which are circularised by selecting the ligation template, in other words by providing an appropriate ligation template (ligation oligonucleotide) which is able to select which monomer unit is circularised. It will be understood in this respect that the ligation templated may be designed to hybridise selectively or preferentially to a selected monomer unit, which will have a different sequence (or more particularly different end sequences) to other monomer units. The monomer unit will comprise at its respective 3' and 5' ends regions of complementarity to corresponding cognate complementary regions (or binding sites) in the ligation template, which may be adjacent where the ends are directly ligated to each other, or non-adjacent, with an intervening "gap" sequence, where indirect ligation is to take place.

The first RCA product may be the product of a primary (i.e. initial) RCA reaction, or it may be the product of a further or later RCA reaction. The second RCA reaction may be a secondary or further, or later, RCA reaction. It will thus be understood that the method of the invention may involve multiple, successive rounds of RCA, e.g. two, three, four or more, wherein in each round the reaction product of a previous round of RCA is monomerised and the monomer units thereof circularised and used as RCA template. Expressed in other words, the method of the invention may comprise repeating steps (a), (b), (c) and (d), and in particular steps (b) to (d) one or more times.

The first RCA product in step (a) is single-stranded. More particularly in step (a) the first RCA product is provided in single-stranded form. This does not preclude, however, that to provide the cleavage sites for the cleavage step (b) oligonucleotides may be hybridised to the single stranded RCP product to provide or create double stranded cleavage sites or cleavage recognition sites (recognition sites for cleavage enzymes). As will be described in more detail below double-stranded cleavage or recognition sites may be provided by separately hybridised "cleavage oligonucleotides" (e.g. restriction oligonucleotides) or by regions of self-complementarity within the first RCA product (e.g. within the monomer repeat) which hybridise together to form hairpin (stem-loop) structures, the double stranded region of which contains a cleavage or recognition site.

The first RCA product may be the direct product of a first RCA reaction (i.e. the concatemer that directly results from the first RCA) or it may be an indirect product, in other words it may be copy or amplicon of the direct first RCA product. For example, a separate amplification step may be carried out on the direct first RCP. This may for example be a PCR step, and PCR primers may be used which are designed to select a portion of the direct first RCP for further amplification. Thus the first RCP may be a portion or a copy of a portion of the direct first RCP. This may have utility in multiplex procedures where a single set of PCR primers may be used to amplify multiple sequences (RCPs) in parallel in order to select a portion of the first RCP for further amplification.

In the method of the invention a primer is required for the second RCA reaction. It may be separately provided, for example after circularisation of the monomer units. Thus the monomer units may comprise a primer binding site for the second RCA primer. A binding site for the second RCA primer may be provided in a region of the monomer unit which is different or separate from the regions which bind to the ligation template. Alternatively, the ligation template may serve as the second RCA primer.

The method of the invention may be homogenous or heterogeneous. That is, it may be performed in solution, without a solid phase or support (i.e. without immobilisation of any reaction components) or it may be performed in an immobilised or solid phase-based format. Immobilisation may occur at various stages of the method, and for example it is not a requirement of a solid-phase based format that there is immobilisation at all stages or steps of the method. For example, the first RCA product may be immobilised, but following cleavage of the product, free monomer units are released. Alternatively or additionally, the primers used for the second RCA (which may be the ligation templates for circularisation of the monomer units) may be immobilised or provided with means for immobilisation. In further embodiments the released monomer units may be hybridised to immobilised capture probes. Use of a heterogeneous, immobilised format allows washes to be readily performed, and hence for example allows for ready removal of unligated monomer units (e.g. by stringent washing after ligation step (c) to remove any unligated probes), and/or other unreacted reaction components added, or spurious unwanted reactions, not physically attached to the surface. Thus, a heterogeneous, or solid phase-based method may readily be performed sequentially.

One of the advantages for the present invention is that the second RCA may be initiated whilst the first RCA in ongoing, or in other words, as soon as the first RCA product has started to form. This leads to the advantage of faster signal generation. Thus signal amplification might optimally proceed as $v^2/2$, compared to where v is the rate of nucleotide incorporation by the polymerase, compared to v for a single RCA, and hence at a multiple of the rate at which new RCA products are generated. This can speed up any RCA-dependent protocol, and may be of particular value for rapid detection assays. Further increases of signal strength or speed or both are possible with a further round of RCA initiating off the second RCA reaction product and so forth (e.g. a third, fourth, fifth . . . . generation of RCA).

Thus, in one embodiment, the method of the invention may include as step (a) the step of generating a first RCA product, (or performing a first RCA reaction to produce a first RCA product). Steps (b), (c) and (d) may take place as soon as the first RCA product starts to form. Accordingly, steps (a) and/or (b) and/or (c) and/or (d) may be performed substantially simultaneously. Accordingly, in certain embodiments the reagents for the cleavage step and circularisation step may be added directly to the reagents for the first RCA reaction. Alternatively, they may be added once the first RCA product has formed (i.e. as noted above the cleavage and ligation steps may be performed in combination. It may further be possible to combine the second RCA reaction.

The first RCA product may be derived from the RCA of any nucleic acid (e.g. DNA or RNA) circle, or indeed the circle may be of any modified nucleic acid, as long as it is capable of templating a RCA reaction. The circle (first RCA template) may for example be a reporter DNA circle, for example from any RCA-based detection assay which uses or generates a nucleic acid circle (circular nucleic acid molecule) as a reporter for the assay. Thus, the a first RCA template for generation of the first RCA product may simply be provided as a reporter and may for example comprise a tag or identifier sequence, e.g. a barcode sequence, which identifies, tags or "labels" (i.e. "marks") the reporter. Alternatively, the first RCA product may be the product of an immunoRCA or a proximity probe assay in which a circular nucleic acid molecule is generated, for example as discussed above, or it may be obtained by RCA of a circularised padlock probe or molecular inversion probe (see e.g. US 2013 0224729). Such probes may also comprise tag or identifier sequences etc. Further alternatively, the first RCA template used to generate the first RCA product may be a circularised target nucleic acid molecule (e.g., an analyte or any desired or selected nucleic acid molecule). Circularisation of target nucleic acid molecules using circularisation adaptors (so-called "Selectors") is described in WO 99/049079, WO 2003/012119 and WO 2005/070630. Generation of circular molecules which might be used as first RCA templates for the generation of the first RCA product is also described in U.S. Pat. Nos. 7,989,166, 5,854,033 and 8,518,640. Any method known and described in the art for generating a circular nucleic acid molecule, and in particular a circular nucleic acid molecule for use in RCA, may be used to provide the first RCA template from which the first RCP is generated.

To reduce the size of the monomer unit some sequence must be removed, that is a part or portion of the sequence of the (e.g. one or more) monomer repeat(s) from which the monomer unit is derived. The first RCA template and hence the first RCP may contain certain regions or sequences which are not necessary for downstream applications e.g. for detection in a detection assay, or for subsequent analysis e.g. for sequencing. Generally speaking, the cleavage reaction may be designed to remove any unnecessary or undesired sequence, for example sequences which are not necessary for downstream analysis or application, but to retain the sequence(s) which are necessary for such applications or analysis. For example, for detection it may be necessary to detect only a tag or sequence identifier region or portion, and for analysis (e.g. sequencing) it may be necessary only to analyse certain parts of the first template molecule (or its complement in the RCP). Cleavage is performed so as to retain such sequence(s) in the reduced monomer unit and/or to generate reduced-length monomer units which contain such sequence(s). For example a target sequence e.g. fragment may be "captured" by circularisation with a circularisation adapter (a so-called "Selector"), and it is necessary only to analyse only the captured sequences and not sequences derived from the adaptor. Analogously, sequences for analysis may be "captured" by using gap-fill embodiments of padlock probes or molecular inversion probes, wherein a sequence representative of (e.g. corresponding to or complementary to) the sequence of interest in a target is incorporated into a circularised probe molecule, and only the captured sequence is needed for further analysis. Thus any unnecessary or undesired sequences can be removed. The location of the cleavage sites in the first RCP may be selected or designed such that such unnecessary or undesired sequences or portions (or regions) of the first RCP (corresponding to, i.e. complementary to, the unnecessary or undesired sequences in the first RCA template) may be removed. In this way a desired part(s) (or portion(s) or region(s)) of the monomer repeat of the first RCP may be selected and used for the generation of the second RCA template.

One typical example of when it is advantageous to decrease the circle is when the detection of the RCA product is performed using so-called molecular bar-codes or tags for proxies of the target (e.g. biological) sequence detected by e.g. a padlock or molecular inversion probe. The sequence used for the identification of the target (namely the sequence in the probe that binds to the target, i.e. the target-complementary region of the probe) is then not necessary once the first round of amplification (first RCA reaction) has been performed. Removal of the target-complementary sequence and only keeping the remaining sequence (e.g. the vector or backbone sequence), whose presence is used as a marker or proxy for the target sequence, allows for faster replication of monomer units in subsequent rounds of RCA. The vector/backbone sequences or more particularly tag or identifier sequences may be detected using any known or convenient means, for example, Amplified Single Molecule Detection (U.S. Pat. No. 7,790,388), hybridization to an array, PCR, quantitative PCR, sequencing or any other method known to those skilled in the art, Another typical example of when it is advantageous to decrease the circle for subsequent rounds of C2CA is when the first circle has been created by means of so called gap-fill between the ends of a vector, using e.g. a padlock or Molecular Inversion Probe. The purpose of performing a gap-fill circularization could be to capture the sequence information between two specific ends of a genomic sequence (e.g. as described in Porreca et al, Nature Methods, Vol. 4 No. 11 November 2007, 931-937). The gap is usually between 1-300 nt long, e.g. between 2 to 20 nt, 20-100 nts or 50-300 nts. To be able to form the circle the vector, containing the two ends that are complementary to target sequences 1 to 300 nt apart, must be of a certain length and in the C2CA this causes unnecessary sequences to be amplified in the subsequent rounds, especially when the purpose is to investigate the nature of the captured sequence by e.g. sequencing. The present invention allows only e.g. the gap-filled part to be selected for subsequent rounds of C2CA, or any other part or combination of parts of the created circle.

Similarly, other circles may be created (for use as first RCA templates) which contain various introduced features or sequence elements, only certain of which may be needed or desired for downstream or subsequent analysis or application. Thus, particular parts or regions of the RCPs resulting from such circles may be selected to form the second RCA templates (circularised monomer units) for the C2CA reaction of the present invention. For example, the formation of nucleic acid circles containing many different features is described in Dramnac et al, Science 1 January 2010: Vol. 327 no. 5961 pp. 78-81 and such circles may be used for so-called nanoball sequencing wherein self-assembling DNA nanoarrays for sequencing are generated. Parts of such circles can be selected for future efficient amplification of only the relevant/necessary part of the sequence. The subsequent rounds of RCA can then be improved in the number of copies produced per minutes of the selected regions, as well as producing smaller DNA nanoballs. This latter feature may be beneficial for improving number of sequences able to be resolved per $mm^2$ of surface.

Many different means of selecting only a part or parts of the monomer repeats in the first RCA product for subsequent amplification can be envisioned. In many cases, this may be achieved by selecting appropriate means of cleavage and by appropriate design and location of cleavage and/or cleavage recognition sites, accordingly to principles and procedures well known and described in the art. Generally speaking and advantageously cleavage will take place by enzymatic means. Thus cleavage enzymes may be used for the cleavage, e.g. restriction enzymes, and enzymatic cleavage (e.g. restriction) sites or recognition sites for cleavage enzymes may be provided in the first RCP. Whilst restriction enzymes (restriction endonucleases) represent a possible choice of cleavage enzyme and indeed may be used in a number of embodiments of the invention, other cleavage enzymes may also be used, including for example an exonuclease or a structure-specific endonuclease (e.g. FLAP endonuclease), or indeed deoxyribozymes (DNAzymes). In certain embodiments, described further below, in which a nicking site (within a double-stranded self-complementary portion) is included in the first RCA product a nickase may be used as the cleavage enzyme. In this regard as will be discussed in more detail below, sequences corresponding to deoxyribozymes may be engineered or incorporated into the first RCP, and may act, e.g. upon provision of activating or suitable conditions for the deoxyribozyme, to cause self-catalysed cleavage of the first RCP into monomer units.

Accordingly the first RCA template may contain the complement of a cleavage site or cleavage enzyme recognition site or auto-catalytic cleavage enzyme (e.g. of a deoxyribozyme), and thus lead to the generation of a cleavage site, recognition site or deoxyribozyme in the first RCP.

As noted above, the RCP is single-stranded but a double stranded cleavage or recognition region may be provided either by intramolecular hybridisation of two self-complementary regions in the RCP (i.e. by hairpin or stem-loop/ stem-like structures) or by intermolecular hybridisation of a complementary oligonucleotide (a so-called cleavage oligonucleotide) to form the cleavage/recognition site.

It will be understood that to select a particular region of the first RCP for cleavage to form a monomer unit, in many embodiments two cleavage sites may be provided e.g. flanking the selected sequence. By cleavage at such sites the selected sequence or region may be released. Thus, a monomer repeat may comprise two cleavage sites or two cleavage recognition sites. In particular, a monomer repeat may be cleaved at two sites, and an intervening monomer unit may thus be generated. Analogously more than two (e.g. three or more) cleavage sites may be provided to result in the generation of different monomer units. Such two or higher multiple cleavage sites may be provided by hairpin/stem-like structures and/or by hybridised cleavage oligonucleotides.

Alternatively, a single cleavage site may be provided per monomer repeat. In such a system the released monomers may, as noted above, be reduced in size in size in a separate step. For example, a substrate for a structure-specific cleavage enzyme e.g. a FLAP endonuclease may be created by hybridisation of a released monomer to a ligation template which hybridises at one of its ends to one end of the monomer and at the other of its ends to an internal sequence of the monomer to leave a protruding end sequence (e.g. a protruding 5' end) which may be removed by digestion with the structure-specific enzyme (or invasion-type restriction digestion). Such digestion results in two ends of the cleaved monomer unit being juxtaposed for ligation, directly or indirectly, on the ligation template to form a circularised molecule, as described for example in U.S. Pat. No. 8,053, 188. Alternatively, rather than using a structure-specific enzyme, an exonuclease may be used to remove the protruding end, or even simply to reduce the size of the monomer unit.

In other embodiments where a single cleavage site is included per monomer repeat a sequence or region may be removed as part of the cleavage step. For example this may be achieved by using a hairpin having a stem and loop structure to provide the cleavage site; cleavage of the hairpin may result in release of loop part of the stem-loop structure of the hairpin, which may be removed, thereby shortening the remaining monomer units resulting from the cleavage. Alternatively, or additionally, the loop part may represent a (different) monomer unit.

Thus, more generally hairpin or stem-loop structures may be used to provide cleavage sites which allow a part of the cleaved sequence to be removed e.g. the loop part. Thus a monomer repeat may comprise one or more e.g. two or more hairpin structures which provide the cleavage sites. The double-stranded stem part of the hairpin provides the cleavage or recognition site, and it will accordingly be understood that in some embodiments the stem-like structure may not have a loop part.

Restriction enzymes may conveniently be used to cleave double-stranded cleavage sites, whether provided by hairpin/stem-like structures or by separately hybridised restriction oligonucleotides. Different types of restriction enzymes may be used, e.g. enzymes which cleave at or within their recognition sites, or at cleavage sites separate to the recognition sites (e.g. type II restriction enzymes). Restriction enzymes may recognise palindromic and non-palindromic sequences and different such sites may be incorporated to result in the generation of monomer units comprising selected parts of the RCP/monomer repeat sequences. For example palindromic restriction sites may be included in the stem regions of hairpin/stem-like structures.

In other embodiments the first RCP may be designed (or more particularly the first RCA template may be designed to result in an RCP) such that released monomer units are able to hybridise into an "open-circle" structure capable of self-templated ligation, as described for example in U.S. Pat. No. 8,080,393. This obviates the need to provide an external ligation template for the circularisation step.

As noted above, depending on the cleavage sites, different regions of the first RCP may be released resulting in different monomer units. Certain released sequences or regions may be discarded as discussed above. However in other cases it may be desirable to retain all or more of the released molecules or monomer units. The different monomer units released will generally have different sequences and hence different monomer units may be selected by being selectively circularised using ligation templates designed to "match" (i.e. be complementary to the ends of) the desired selected monomer unit.

A non-limiting description of particular embodiments now follows. It will be understood that different combinations of various features of these particular embodiments are possible and may be used according to the present invention.

Figure 2:
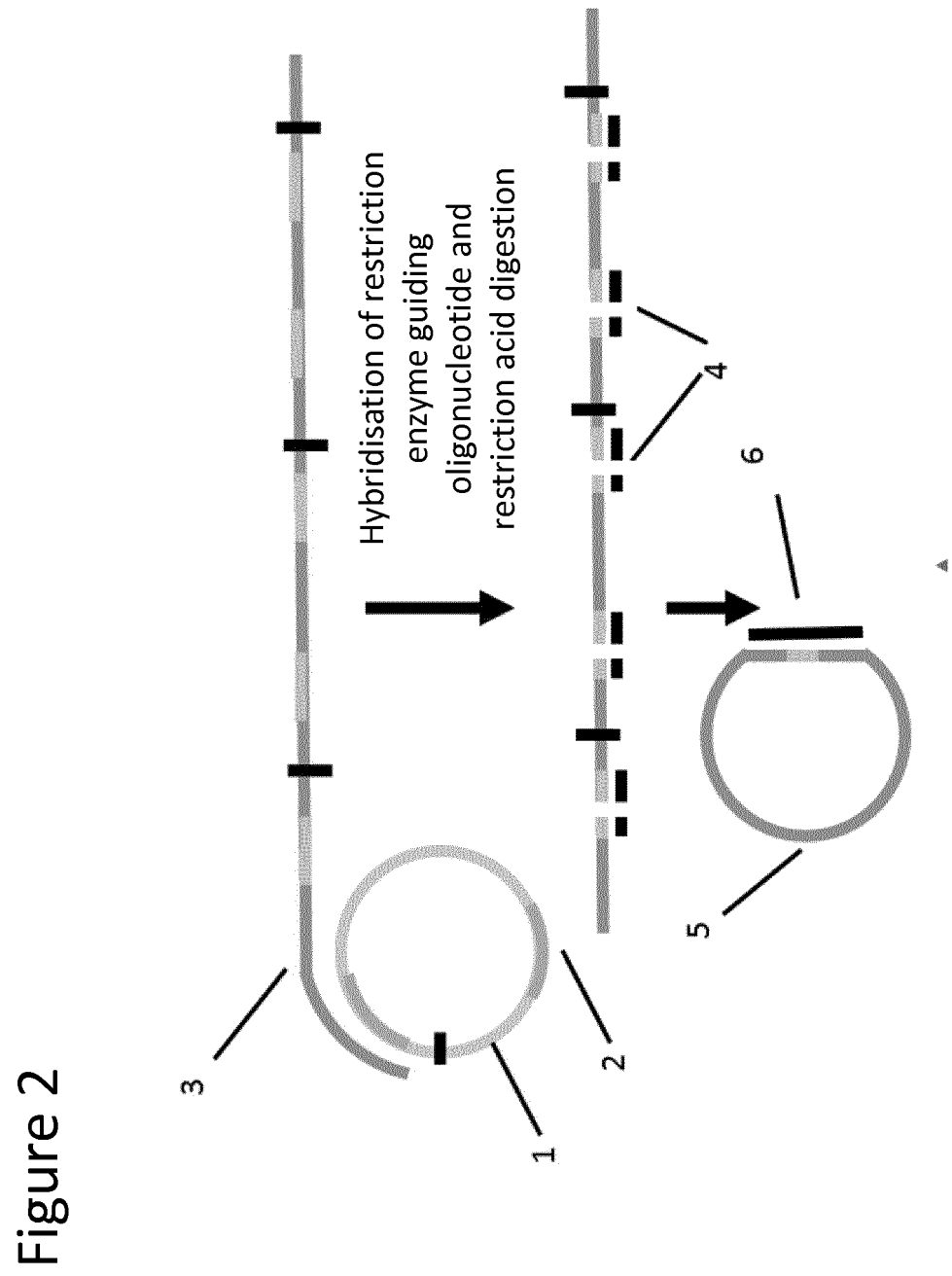

FIG. 1 shows an embodiment using self-templated digestion (cleavage) without external cleavage oligonucleotides by means of stem-like structures formed within each RCA monomer repeat. Thus each monomer repeat contains two regions which are complementary to one another and may hybridise together to form a hairpin or stem-like structure. The self-complementary, palindromic, regions contain a recognition site for a palindromic restriction enzyme. After cleavage using a palindromic restriction enzyme, monomer units are released from which the loop part of the hairpin structures has been removed. These may be discarded. Circularisation of the shortened monomer units may then take place, using an external ligation template, which hybridises to the ends of the monomer unit and which may also serve as primer for next generation RCA The ligation template and/or ligase may be added at this time or may be included in initial reaction mixture. The sequence designed to be in the loop of the stem-loop is removed and the next generation of the circle thus becomes smaller. For the next round of C2CA the principle of the original C2CA is used Another alternative shown in FIG. 2 is that the first probe is designed to contain a set of repetitive sequences so that using one restriction oligonucleotide the first RCA product is cut twice or more per monomer instead of once as in traditional C2CA. In other words, each monomer repeat contains two cleavage sites (restriction sites as shown). The restriction sites may be identical, as shown, so that the same restriction oligonucleotide may be used to create the restriction sites. In alternative embodiments, different restriction sites could be used. Advantageously, the same restriction oligonucleotide may be used as ligation template for circularisation, as described in the original C2CA amplification method of WO 03/12119. In such an embodiment, as the cleavage site is a repeated sequence the same oligonucleotide as used for restriction enzyme digest can be used for ligating the new, shorter molecule as in traditional C2CA (see FIG. 2). Depending on the length of the repeated sequences (cleavage sites) it can be designed so that only a short part of the external oligonucleotide used for generating the restriction cleavage site (rendering the sequence double stranded, and thus a substrate for a restriction enzyme) is used for the cleavage of the RCA product. Once the product is cleaved the intact (non-cleaved) external oligonucleotide is complementary to the two ends of one of the new fragments and thus is preferentially able to circularize that fragment. In this respect, the restriction/ligation template oligonucleotide may be used in excess (particularly in excess over the number of cleavage sites) or more oligonucleotide may be added after cleavage. It is also possible to circularize both (or more if more than two repeats per circle) of the generated fragments using the same oligonucleotide used for restriction enzyme digest as in traditional C2CA. It is also possible to have one oligonucleotide for the restriction enzyme digestion and another for circularization of the selected part of the first RCA product i.e. to use separate restriction oligonucleotides and ligation templates. The produced circle will thus be a shorter circle than the circle used for generating the first RCA product. If more than one fragment of the first RCA product is selected for further amplification the circles can be amplified during subsequent C2CA steps in parallel and either one or more of the circularized parts of the RCA product may be detected, e.g. in a later stage. This has the potential to increase the amplification efficiency even further.

Figure 3:
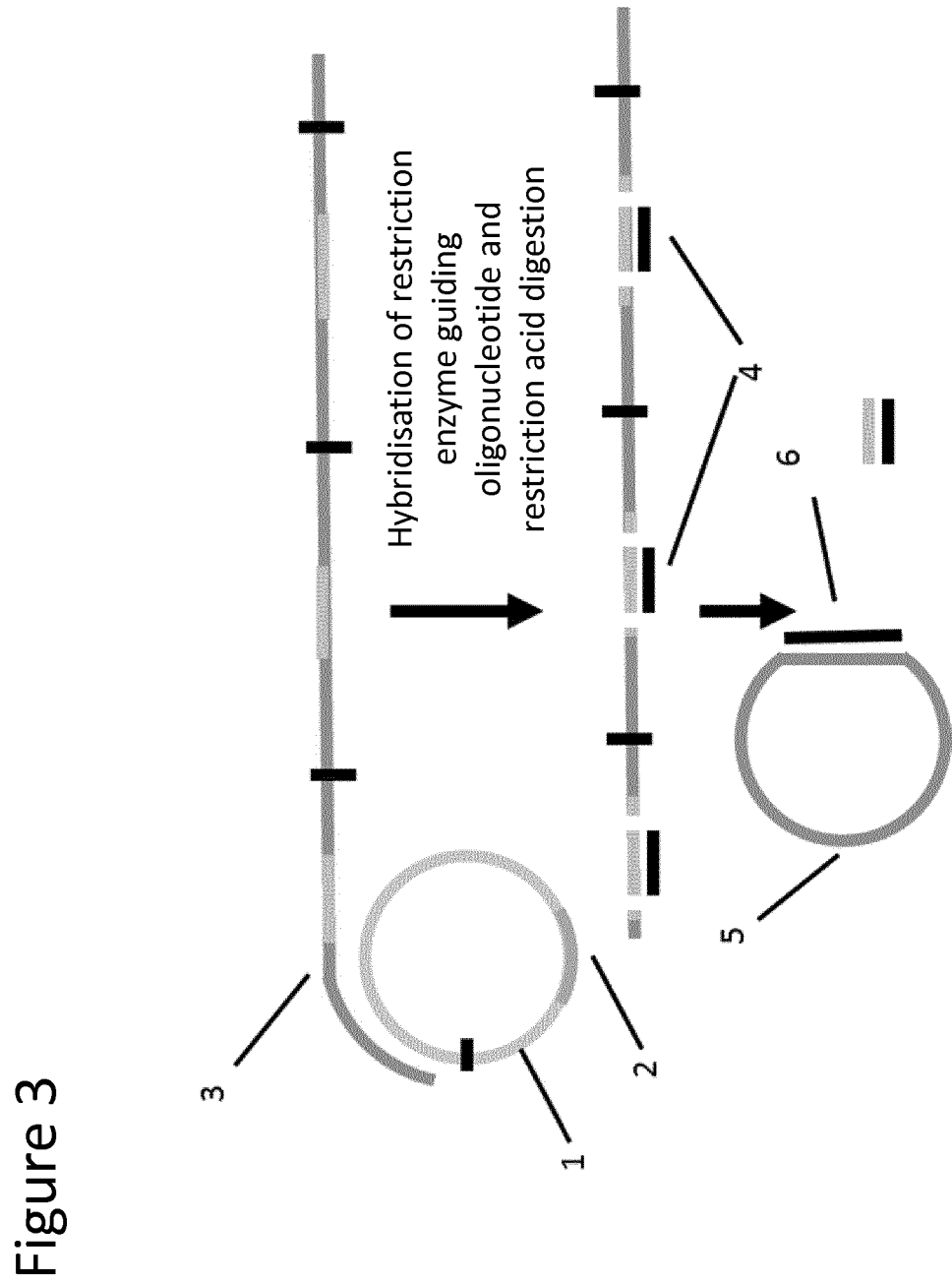

In a third embodiment, as shown in FIG. 3, a type II subtype of restriction enzyme may be used, which cleaves outside its recognition sequence. Thus the first RCP may be designed to contain within each monomer a recognition sequence for a type IIs restriction enzyme. Upon hybridization to its cognate complementary restriction oligonucleotide (i.e. an oligonucleotide sequence targeting the recognition sequence for the restriction enzyme plus flanking regions) a double stranded substrate for the type IIs restriction enzyme is formed, and the first RCP may then be cleaved using the type II subclass type of restriction enzyme where the cleavage is directed outside the recognition sequence of the enzyme itself. Segments (i.e. monomer units), each containing a selection of the sequence included in the first circle (i.e. RCA template) are then created (more particularly the segments (monomer units) contain a complement of a selected sequence of the first RCA template). The selected part of the first circle (selected monomer unit) can then be joined into a new circle (by ligating its ends) using either a second external oligonucleotide (ligation template) that guides the formation of a new circle used in subsequent C2CA steps or the new circle can be joined using the double stranded sticky ends generated during the restriction enzyme digest. This latter variant requires that the sequence still hybridized to the part of the circle (monomer unit) that has been selected for further amplification is sufficiently long to remain hybridized after the cleavage step. The oligonucleotide template used for ligation may also function as the primer for the subsequent RCA.

It is easily envisioned that it is possible to select several different regions within each monomer repeat in the first RCA product using any of the methods described above, and to transform each of them into individual new, smaller, molecules suitable for circularization and subsequent C2CA. Each of the new formed circles can be analyzed or detected individually. This is especially interesting if several regions of interest have been inserted or are present in a circle used for the first RCA step to produce the first RCA product that is used for the C2CA.

Figure 4:
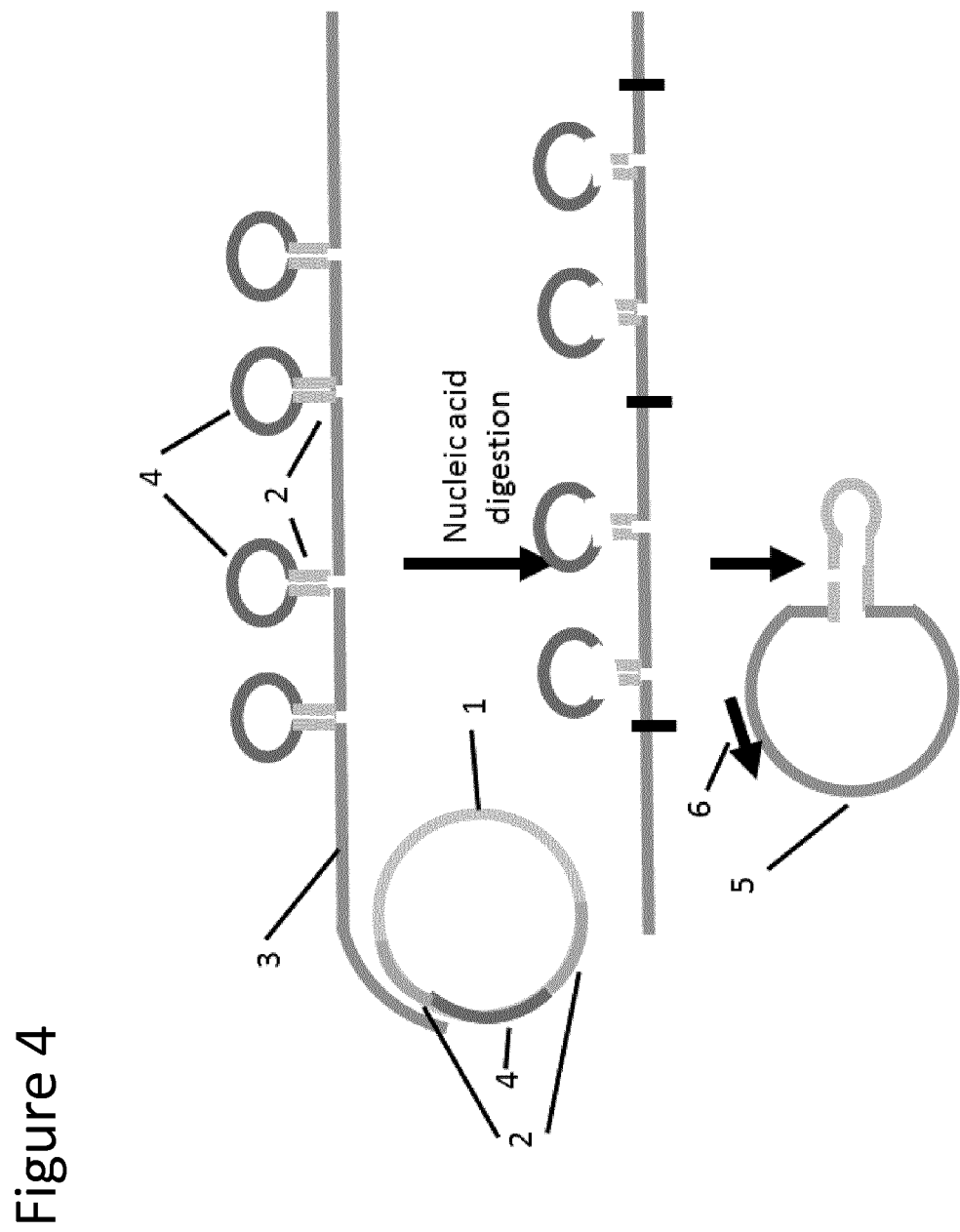

Yet another embodiment is shown in FIG. 4. This uses self-templated ligation of circles as described in U.S. Pat. No. 8,080,393. In U.S. Pat. No. 8,080,393 a modification of the C2CA process is described in which a so-called "nicking cassette" is incorporated into the first RCA template, which results in the generation of a first RCP for the C2CA which comprises nicking sites which may be nicked to monomerise the RCP without the need for an external restriction oligonucleotide. The released monomers are able to hybridise in a self-templated hybridisation reaction to form "open circle" structures the ends of which may be ligated together in a self-templated ligation reaction, i.e. without the need to provide an external ligation template. This format however preserves the original size of the circle in each subsequent amplification step. In the embodiment shown in present FIG. 4, this method is further modified according to the present invention to incorporate two hairpin structures per monomer repeat. In addition to, or in place of, the nicking site, the hairpin structures include in the stem part a restriction cleavage site. Upon restriction cleavage monomer units are released which are reduced in size, as they are degraded into the loop part and a linear part (as shown in FIG. 4). The use of two hairpins per monomer repeat, each with a restriction site, allows the selection of a part of the original sequence. Accordingly by including more than one stem-structure in each monomer repeat, shorter fragments of the original monomeric repeat may be created. Each, or one of the fragments, may be designed to form a self-templating structure and may be ligated to form a new circle used for subsequent rounds of RCA, as in C2CA. Alternatively, after digestion using a restriction enzyme instead, the RCA product is cut into three different types of sequences. The smaller fragment of the original monomer can be so designed that it self-forms into a substrate capable of self-ligating, as described in U.S. Pat. No. 8,080,393, and after that can be used as a template for further rounds of RCA such as in C2CA. To continue the C2CA with this new, smaller circle it is possible to either continue using the self-templating variant of the C2CA method as described in U.S. Pat. No. 8,080,393, or with a conventional RCA step as in conventional C2CA.

In a further variant of the embodiment described in FIG. 4, only one stem may be present per monomer repeat, as described in U.S. Pat. No. 8,080,393. To reduce the size of the circle in such an embodiment, the system may be designed so that a larger loop is present in the stem (as depicted in present FIG. 1). Digestion using a restriction enzyme produces two fragments, the loop part and the remaining parts of the monomer i.e. a reduced monomer unit. The reduced monomer unit is able to form a structure allowing self-templated ligation, as described in U.S. Pat. No. 8,080,393, and the ligated circle resulting therefrom may be used as the template for a further RCA reaction.

In still further embodiments deoxyribozymes may be incorporated into the sequence of the first RCP, and autocatalytic cleavage of the first RCP by the deoxyribozymes may take place by altering the reaction conditions to favour deoxyribozyme action. Cleavage of a RCA product in this way is described in Gu and Breaker, Biotechniques 54:337-343 (June 2013, FIG. 2.) By designing several DNAzymes per monomer repeat, instead of the single per monomer unit described in Gu and Breaker, it is possible to remove part of the circle for the next round of amplification. The circularisation can be achieved either via template dependent ligation as normal or via self-templated circualrisation as described in U.S. Pat. No. 8,080,393.

As noted above, generation of circles containing only a part of the monomeric units in the first RCA product can also be achieved by as described in U.S. Pat. No. 8,053,188. The monomer units resulting from digestion of the first RCA product are designed so that after hybridization to a complementary oligonucleotide (ligation template) a protruding 5' end is created. The protruding end is removed from the next generation circle via an invasion type restriction digestion as described in U.S. Pat. No. 8,053,188. The resulting new circle is shorter than the first generation RCA template.

It will be appreciated that in some embodiments of the invention restriction enzymes are used, and in particular such embodiments intact restriction oligonucleotides remaining after cleavage might be able to form further, undesirable restriction cleavage sites. To avoid any unwanted such cleavage, a step of inactivating the cleavage enzyme may be included in the method. Accordingly after cleavage step (a) a step of inactivating the cleavage enzyme may be included, for example by heating i.e. heat-inactivating the enzyme. However, such a step may not be desirable in all embodiments, for example where steps (b) and (c) are combined. Accordingly, an inactivation step is not essential according to the invention. As an alternative, reaction conditions may be designed or selected which allow the combination of the cleavage and ligation steps. In particular, it has been found possible to determine such conditions by titrating the ligase and the cleavage enzyme, with a much higher activity of the ligase compared to the cleavage enzyme (e.g. restriction enzyme), shifting the equilibrium towards ligation As generally discussed above, the methods of the invention have a number of applications, including in signal amplification, and hence in any detection method or assay based on detecting an RCA product. Accordingly, in such an embodiment the methods of the invention as defined above may include an additional or further step of detecting a second (and/or further) RCA product. Additionally, the methods of the invention may be used preparatively to synthesise multiple copies of a desired nucleic acid molecule. In such embodiments, the methods may include a further step of recovering or collecting the second or further RCP, or monomer units generated therefrom. In still further applications the method may be used for analysing nucleic acids, for example in sequencing, or in detection of particular sequences or nucleotides (e.g polymorphisms or mutations) in a nucleic acid molecule. For example, the methods may be used to generate or provide substrates or templates for sequencing, in particular for next generation sequencing protocols. Thus in such methods there may be included a further step of analysing (e.g analysing the sequence of) of a second or further RCP or of a monomer unit generated therefrom. Accordingly, the methods of the invention may include a further step of cleaving the second RCA product of step (d) into monomer units and optionally detecting and/or analysing the monomer units. Alternatively, the methods of the invention may include the further step of detecting and/or analysing the second RCA product.

Alternatively viewed, such embodiments may be seen to provide a further aspect of the invention, which may be defined as a method for analysing or detecting a nucleic acid molecule, said method comprising performing a RCA reaction as defined herein and analysing and/or detecting said second RCA product as defined above, and/or a monomer unit derived therefrom.

Advantages of such a method, as noted above, include stronger and/or faster amplification e.g signal amplification. The method thus has particular utility in the detection and/or analysis of any desired assay target or analyte, which may be a target/analyte nucleic acid molecule which may itself by amplified by RCA to form a first RCA product or a target/analyte nucleic acid molecule or any other molecule which may be detected by an assay which uses or generates a circular nucleic acid molecule as an assay reporter or a marker for the assay target/analyte (see above). Such a circle may be the first RCA template used to generate the first RCA product.

Thus the methods of the invention may find utility in the detection or analysis of a nucleic acid molecule in a sample. The nucleic acid molecule may be the target analyte for detection or may be indicative of the presence of the target analyte in a sample. For instance, the nucleic acid molecule may be attached to the target, e.g. a nucleic acid domain of an antibody:nucleic acid conjugate which is bound, directly or indirectly, to the target, e.g. a protein molecule. Similarly, the nucleic acid molecule to be detected may be a nucleic acid molecule generated from the interaction between proximity probes, which are bound to the target analyte, e.g. a protein.

Accordingly, the invention may be seen to provide a method for detecting an analyte in a sample, wherein a first circular RCA template is used or generated (e.g. generated from a nucleic acid analyte or used or generated as a marker for said analyte), a first RCA reaction is performed using said first RCA template to generate a first RCA product, a second RCA reaction is performed as described herein to generate a second RCA product, and said second RCA product or a monomer unit derived therefrom is detected.

The first RCA product may be generated by a first RCA reaction using a first RCA template which may itself be or be derived or generated from: (i) the analyte;(ii) a nucleic acid molecule (e.g. probe) directly or indirectly attached to the analyte; or(iii) indicative of, or a proxy for, (i.e. a marker for) the analyte in the sample.RCA templates, i.e. circular or circularisable nucleic acid molecules, e.g. oligonucleotides, are well known in the art.

A RCA template typically may comprise about 20-1000 nucleotides, e.g. 26-1000, 30-1000, 30-900, 60-900, 40-800, 50-700, 60-600, 70-500, 80-400, 90-300 or 100-200 nucleotides, such as at least 20, 25, 26, 27, 28, 29, 30, 35, 40, 50, 60, 70, 80, 90, 100, 120, 150, 200 or 250 nucleotides. More particularly in the methods of the invention the first RCA template may comprise 20-150, e.g. 20-120, 20-100, 25-150, 25-120, 30-150, 30-120, 30-100, 40-150, 40-120, 40-100 nucleotides.

In the methods of the invention, the number of nucleotides in the second RCA template may be reduced by at least 10, 15, 20, 25, 30, 35, 40, 45, 50% or more compared to the first RCA template. The extent of or % reduction may depend on the size of the first RCA template. The second RCA template may be reduced to any size capable of templating an RCA reaction e.g at least 20, 25, 26, 27, 28, 29 or 30 nucleotides. The second RCA template may comprise a reporter domain, which is a sequence that can be used to detect and/or identify the RCA product, i.e. the primer extension product templated by the RCA template. This is particularly advantageous in multiplex embodiments of the invention, where more than one different first RCA product is subjected to the method e.g. where more than one analyte, e.g. nucleic acid analyte, is detected in a single assay. The second RCA template may comprise a unique "marker" or identification or tag sequence (e.g. a bar-code sequence, such as a site comprising the sequence of a specific detection probe, i.e. the RCA product is complementary to the RCA template and as such detection probes that hybridize to the RCA product will comprise a sequence that is identical to part of the RCA template) to allow the separate detection and/or quantification of each analyte in the sample.

Thus, in multiplex assays each second RCA template may comprise a different reporter domain and each analyte may be detected in parallel (i.e. at the same time), e.g. using oligonucleotides tagged with distinct fluorophores that may hybridise to the complement of the reporter domain. Alternatively, each marker (and therefore each analyte) may be detected using sequential visualisation reactions, wherein each reaction is separated by, e.g. stripping or bleaching steps. Methods of sequential visualisation reactions suitable for using the methods of the invention are known in the art, e.g. Göransson et al., 2009 (A single molecule array for digital targeted molecular analyses.Nucleic Acids Res. 2009 Jan; 37(1):e7), Wählby et al., 2002 (Sequential immunofluorescence staining and image analysis for detection of large numbers of antigens in individual cell nuclei. Cytometry, 47(1):32-41, 2002), which are hereby incorporated by reference.

In some representative embodiments of the invention, multiple analytes may be detected in parallel. In other representative embodiments of the invention, multiple analytes may be detected sequentially. Combinatorial methods of labelling, e.g. ratio labelling, using different combinations and/or ratios of different labels are known in the art and may be used to increase the number of different molecules, and hence different analytes which may detected at one time, or in the same reaction. For example, combinations using different coloured and/or fluorescent labels and/or different ratios of different coloured and/or fluorescent labels may be used. For example, such "colour"-coding with different combinations of coloured and/or fluorescent labels may be used in multiplex assays based on detection by flow cytometry or microscopy.

Alternatively, using lanthanide isotope labels cyToF detection may be used. By way of example, 7 different fluorophores may be grouped into 4 different types. There are 7 different combinations if labelled with only one colour, with 2 colours there are 21 different combinations, for 3 and 4 colours there are 35 different combinations and so on.

The primer for the second RCA comprises a region of complementarity (defined further below) to a part of the second RCA template, which forms a duplex that is sufficiently stable under the conditions of the assay to facilitate RCA template dependent extension of the primer. The primer will generally be at least 5 nucleotides in length, typically at least 6, 8 or 10, usually at least 15 or 16 nucleotides in length and may be as long as 30 nucleotides in length or longer, where the length of the primer will generally range from 5 to 50 nucleotides in length, e.g. from 6, 8 or 10 to 50, 40, 30 or 20, usually from about 10 to 35 nucleotides in length.

A region of complementarity to its cognate or complementary nucleic acid molecule refers to a portion of the nucleic acid molecule that is capable of forming an intermolecular duplex with at least a region of the cognate (complementary) nucleic acid molecule. Subject to the size ranges indicated above, the regions of complementarity will be sufficient to form a stable duplex in the conditions in which the method finds utility. "Complementary" nucleotide sequences will combine with specificity to form a stable duplex under appropriate hybridization conditions. For instance, two sequences are complementary when a section of a first sequence can bind to a section of a second sequence in an anti-parallel sense wherein the 3'-end of each sequence binds to the 5'-end of the other sequence and each A, T(U), G and C of one sequence is then aligned with a T(U), A, C and G, respectively, of the other sequence. RNA sequences can also include complementary G=U or U=G base pairs. Thus, two sequences need not have perfect homology to be "complementary" under the invention. Usually two sequences are sufficiently complementary when at least about 85% (preferably at least about 90%, and most preferably at least about 95%) of the nucleotides share base pair organization over a defined length of the molecule.

The nucleic acid molecules used in the invention (e.g. RCA templates and RCA products, cleavage oligonucleotides, primers and/or ligation templates) may be made up of ribonucleotides and/or deoxyribonucleotides as well as synthetic nucleotide residues that are capable of participating in Watson-Crick type or analogous base pair interactions. Thus, the nucleic acid domains may be DNA and/or RNA or any modification thereof e.g. PNA or other derivatives containing non-nucleotide backbones.

As described above, the methods and probes of the invention may be useful for the detection of any target analyte, wherein if the target analyte is not a nucleic acid molecule, a first RCA template (or indeed a first RCA product) may be viewed as a marker for the analyte. The "analyte", or ultimate detection assay target or objective, may be any substance (e.g. molecule) or entity it is desired to detect.

The analyte is thus the "target" of a detection method of the invention. The analyte may accordingly be any biomolecule or chemical compound it may be desired to detect, for example a peptide or protein, or nucleic acid molecule or a small molecule, including organic and inorganic molecules. The analyte may be a cell or a microorganism, including a virus, or a fragment or product thereof. An analyte can be any substance or entity for which a specific binding partner (e.g. an affinity binding partner) can be developed. Such a specific binding partner may be a nucleic acid probe (for an nucleic acid analyte) and may lead directly to the generation of a first RCA template (e.g. a padlock probe). Alternatively, as discussed above, the specific binding partner may be coupled to a nucleic acid, which may be detected using an RCA strategy, e.g. in an assay which uses or generates a circular nucleic acid molecule which can be the first RCA template.

Analytes of particular interest may thus include nucleic acid molecules, such as DNA (e.g. genomic DNA, mitochondrial DNA, plastid DNA, viral DNA etc.) and RNA (e.g. mRNA, microRNA, rRNA, snRNA, viral RNA etc.), and synthetic and/or modified nucleic acid molecules, (e.g. including nucleic acid domains comprising or consisting of synthetic or modified nucleotides such as LNA, PNA, morpholino etc.), proteinaceous molecules such as peptides, polypeptides, proteins or prions or any molecule which includes a protein or polypeptide component, etc., or fragments thereof. The analyte may be a single molecule or a complex that contains two or more molecular subunits, e.g. including but not limited to protein-DNA complexes, which may or may not be covalently bound to one another, and which may be the same or different. Thus in addition to cells or microorganisms, such a complex analyte may also be a protein complex or protein interaction. Such a complex or interaction may thus be a homo- or hetero-multimer. Aggregates of molecules, e.g. proteins may also be target analytes, for example aggregates of the same protein or different proteins. The analyte may also be a complex between proteins or peptides and nucleic acid molecules such as DNA or RNA, e.g. interactions between proteins and nucleic acids, e.g. regulatory factors, such as transcription factors, and DNA or RNA.

Identification of RNA may be accomplished via cDNA, for instance by using a suitable reverse transcriptase (RT) primer. A RT primer may be used, binding to the target RNA at a site which is upstream of a recognition site for a probe (e.g. a padlock probe), (more particularly upstream of the complement of the recognition site in the cDNA). Extension of the primer produces a cDNA molecule comprising the probe recognition site, and the probe may be used to report the presence and identity of the cDNA, and therefore of the RNA molecule. It may thus be possible to avoid the requirement to replicate an entire RNA molecule in order to identify it; it is only necessary to extend the primer to cover the probe recognition site. Thus the time required for the initial extension step may be reduced. Extension may be performed for 10, 20, 30, 40, or 50 seconds, or 1, 2, 3, 4, 5, or 10 minutes to reduce the length of time required to identify an RNA molecule in a sample.

All biological and clinical samples are included, e.g. any cell or tissue sample of an organism, or any body fluid or preparation derived therefrom, as well as samples such as cell cultures, cell preparations, cell lysates etc. Environmental samples, e.g. soil and water samples or food samples are also included. The samples may be freshly prepared or they may be prior-treated in any convenient way e.g. for storage.

Representative samples thus include any material which may contain a biomolecule, or any other desired or target analyte, including for example foods and allied products, clinical and environmental samples. The sample may be a biological sample, which may contain any viral or cellular material, including all prokaryotic or eukaryotic cells, viruses, bacteriophages, mycoplasmas, protoplasts and organelles. Such biological material may thus comprise all types of mammalian and non-mammalian animal cells, plant cells, algae including blue-green algae, fungi, bacteria, protozoa etc. Representative samples thus include whole blood and blood-derived products such as plasma, serum and buffy coat, blood cells, urine, faeces, cerebrospinal fluid or any other body fluids (e.g. respiratory secretions, saliva, milk, etc.), tissues, biopsies, cell cultures, cell suspensions, conditioned media or other samples of cell culture constituents, etc. The sample may be pre-treated in any convenient or desired way to prepare for use in the methods and uses of the invention, for example by cell lysis or purification, isolation of the analyte, etc.

The detection of the target analyte depends upon the presence of an analyte in a sample, which leads to the generation of the first RCA product. A second RCA product is then generated according to the invention, and can be detected in order to detect the analyte. As discussed above, the second RCA product can lead to a much stronger and/or faster signal.

It will thus be apparent that the present invention provides a method of detecting an analyte in a sample, wherein first circular RCA template is used or generated as a marker for said analyte, or comprises or is generated from a nucleic acid analyte, said method comprising:
  i) performing a first RCA reaction using said first RCA template to generate a first RCA product;
  ii) performing steps (a) to (d) as defined above to generate a second RCA product;
  iii) detecting said second RCA product or a monomer unit derived therefrom, thereby to detect the analyte.

In a particularly preferred embodiment, said first RCA template may include a tag sequence or captured sequence, wherein the complement thereof is retained in the reduced monomer unit and which (or its complement) is detected in the second or subsequent RCP or monomer unit derived therefrom.

Thus, upon the addition of appropriate polymerase and ligase enzymes, the presence of analyte in the sample may be detected by rolling circle amplification (RCA) of the second RCA template, i.e. by detecting the second RCA product, or optionally a monomer unit derived therefrom. The concatemeric RCA product may provide the "signal" for detection of the analyte. Said signal may be detected by any appropriate means known in the art (see below for further examples) and as taught in U.S. Pat. No. 7,320,860, e.g. by hybridisation of labelled probes to a reporter domain sequence, which is repeated throughout the concatemeric RCA products.

The term "detecting" is used broadly herein to include any means of determining the presence of the analyte (i.e. if it is present or not) or any form of measurement of the analyte. Thus "detecting" may include determining, measuring, assessing or assaying the presence or absence or amount or location of analyte in any way. Quantitative and qualitative determinations, measurements or assessments are included, including semi-quantitative. Such determinations, measurements or assessments may be relative, for example when two or more different analytes in a sample are being detected, or absolute. As such, the term "quantifying" when used in the context of quantifying a target analyte(s) in a sample can refer to absolute or to relative quantification. Absolute quantification may be accomplished by inclusion of known concentration(s) of one or more control analytes and/or referencing the detected level of the target analyte with known control analytes (e.g. through generation of a standard curve). Alternatively, relative quantification can be accomplished by comparison of detected levels or amounts between two or more different target analytes to provide a relative quantification of each of the two or more different analytes, i.e., relative to each other.

The term "hybridisation" or "hybridises" as used herein refers to the formation of a duplex between nucleotide sequences which are sufficiently complementary to form duplexes via Watson-Crick base pairing. Two nucleotide sequences are "complementary" to one another when those molecules share base pair organization homology. Hence, a region of complementarity refers to a portion of a nucleic acid molecule that is capable of forming an intra- or intermolecular duplex, i.e. either a duplex within the same molecule (a hairpin or stem-like structure) or a duplex with a different molecule. These terms are also used to refer to base pair interactions which are analogous to Watson-Crick base pairing, including Hoogsteen base pairing which is a rarely observed variation of base pairing which also allows for a third strand to wind around a double-helix assembled in a Watson-Crick pattern to form a triplex.

A cleavage recognition site is a sequence that is recognised by a cleavage enzyme, i.e. the cleavage enzyme is capable of interacting specifically with the cleavage recognition site, wherein said interaction results in the cleavage of a nucleic acid molecule. In some embodiments as described herein the cleavage enzyme may cleave the nucleic acid molecule at the cleavage recognition site, i.e. the cleavage recognition site may be a cleavage or cleavable site. In other embodiments the cleavage enzyme may cleave at a position directly or indirectly adjacent to the cleavage recognition site, i.e. the cleavage or cleavable site may be distinct from the cleavage recognition site. Hence, the first RCA product may according to the invention comprise cleavage recognition sites and cleavage/cleavable sites as separate features. In other embodiments, the cleavage recognition sites may be cleavage/cleavable sites.

"Cleavage" is defined broadly herein to include any means of breaking a nucleotide chain (i.e. a nucleotide sequence). Cleavage may thus involve breaking a covalent bond. This may involve cleavage of nucleotide chain (i.e. strand cleavage or strand scission), for example by cleavage of a phosphodiester bond.

As noted above, in some embodiments the cleavage recognition site (or cleavage site) is in a hairpin or stem-like structure.

In other embodiments the first RCA product may hybridise to a "cleavage oligonucleotide" or a "restriction oligonucleotide to provide a cleavage site e.g. an endonuclease recognition site.

As described above, in particular embodiments it may be useful to utilise a type II restriction endonuclease recognition sequence, and optionally a cleavage domain. Some type II restriction endonucleases, e.g. type IIS enzymes, may find particular utility in the methods of the invention. Type II restriction endonucleases either cleave within a specific cleavage recognition site or at an adjacent site (a cleavage domain), wherein the adjacent site may be a specific distance from the cleavage recognition site (e.g. a type IIS enzyme) and/or may comprise an additional cleavage recognition site (e.g. a type IIE enzyme).

In some embodiments wherein the first RCP contains a nicking site within a self-complementary duplex structure a nickase enzyme may be used to cleave the RCP, which cleaves only one strand in the duplex of the hairpin structure. Thus, the cleavage site may be a site for a nickase enzyme. Nickases are endonucleases which cleave only a single strand of a DNA duplex. Some nickases introduce single-stranded nicks only at particular sites on a DNA molecule, by binding to and recognizing a particular nucleotide recognition sequence, i.e. a cleavage recognition sequence. Some nickases introduce single-stranded nicks at mis-match positions in a duplex. Hence, in some embodiments, the cleavage recognition site may be formed when the duplex of the hairpin structure comprises a mis-match. A number of naturally-occurring nickases have been discovered, of which at present the sequence recognition properties have been determined for at least four. Nickases are described in U.S. Pat. No. 6,867,028, which is herein incorporated by reference in its entirety and any suitable nickase recognition site may be used in the probes and methods of the invention.

In some embodiments of the methods of the invention that utilise a nickase enzyme, the nickase enzyme is removed from the assay or inactivated following cleavage to prevent unwanted cleavage of ligation products.

In further embodiments of the invention an exonuclease enzyme may be used to reduce the length of the monomer unit. The exonuclease enzyme may have 5' or 3' exonuclease activity depending on the orientation of the monomer unit to be reduced. Suitable exonuclease enzymes are well known in the art.

Exonucleases may also be used in the methods of the invention to remove unligated (uncircularised) monomer units, or unwanted parts or molecules released from cleavage of the first RCA product, (e.g. loop parts), if desired.

Reaction conditions for the various steps of the method, namely cleavage, ligation and RCA steps are well known in the art. Thus according to known or standard procedures the first RCA product may be subjected to enzymatic cleavage. The monomer units thereby released, or selected monomer units, may be circularised by ligation. This may include incubating a reaction mixture containing the monomer units with a ligation template if necessary under conditions suitable for ligation. As discussed above the ligation step may be performed substantially simultaneously with the cleavage step (i.e. the steps may be combined). Once a primer/RCA template complex has formed, the primer may be extended using the second RCA template as a template for polymerisation. In some embodiments wash steps may be included between the ligation step and the generation of the second RCP, or before detection of the second RCA product, e.g. the second RCA product may be captured or immobilised on a solid support or substrate, which may be subjected to washing.

In general, any convenient protocol that is capable of detecting the presence of an RCA product may be employed to detect the second RCA product. The detection protocol may or may not require a separation step.

As is known in the art, in template-directed ligation ligases catalyse the formation of a phosphodiester bond between juxtaposed 3'-hydroxyl and 5'-phosphate termini of two immediately adjacent nucleic acids when they are annealed or hybridized to a third nucleic acid sequence to which they are complementary (i.e. a ligation template). Any convenient ligase may be employed, where representative ligases of interest include, but are not limited to: temperature sensitive and thermostable ligases. Temperature sensitive ligases include, but are not limited to, bacteriophage T4 DNA ligase, bacteriophage T7 ligase, and E. coli ligase. Thermostable ligases include, but are not limited to, Taq ligase, Tth ligase, Ampligase® and Pfu ligase. Thermostable ligase may be obtained from thermophilic or hyperthermophilic organisms, including but not limited to, prokaryotic, eukaryotic, or archael organisms. Certain RNA ligases may also be employed in the methods of the invention.

A suitable ligase and any reagents that are necessary and/or desirable may be combined with the reaction mixture and maintained under conditions sufficient for ligation of the hybridized oligonucleotides to occur. Ligation reaction conditions are well known to those of skill in the art. During ligation, the reaction mixture in certain embodiments may be maintained at a temperature ranging from about 4° C. to about 105° C., about 4 to about 80° C., such as about 10 to about 70° C., about 15 to about 60° C., typically such as from about 20° C. to about 37° C. for a period of time ranging from about 5 seconds to about 16 hours, such as from about 1 minute to about 1 hour. In yet other embodiments, the reaction mixture may be maintained at a temperature ranging from about 35° C. to about 45° C., such as from about 37° C. to about 42° C., e.g., at or about 38° C., 39° C., 40° C. or 41° C., for a period of time ranging from about 5 seconds to about 16 hours, such as from about 1 minute to about 1 hour, including from about 2 minutes to about 8 hours. In a representative embodiment, the ligation reaction mixture includes 50 mM Tris pH7.5, 10 mM MgCl$_2$, 10 mM DTT, 1 mM ATP, 25 mg/ml BSA, 0.25 units/ml RNase inhibitor, and T4 DNA ligase at 0.125 units/ml. In yet another representative embodiment, 2.125 mM magnesium ion, 0.2 units/ml RNase inhibitor; and 0.125 units/ml DNA ligase are employed.

It will be evident that the ligation conditions may depend on the ligase enzyme used in the methods of the invention. Hence, the above-described ligation conditions are merely a representative example and the parameters may be varied according to well-known protocols. For example, a ligase that may be utilized in the methods of the invention, namely Ampligase®, may be used at temperatures of greater than 50° C. However, it will be further understood that the alteration of one parameter, e.g. temperature, may require the modification of other conditions to ensure that other steps of the assay are not inhibited or disrupted, e.g. binding of the probe to the target nucleic acid molecule. Such manipulation of RCA assay methods is routine in the art.

The next step of the method following the ligation step is to generate the second RCA product. Rolling-circle amplification (RCA) is well known in the art, being described in Dean et al., 2001 (Rapid Amplification of Plasmid and Phage DNA Using Phi29 DNA Polymerase and Multiply-Primed Rolling Circle Amplification, Genome Research, 11, pp. 1095-1099), the disclosures of which are herein incorporated by reference. The RCA primer is employed in a primer extension reaction, i.e. the RCA primer is extended on the second RCA template to generate the second RCA product, being a single concatemeric product. The RCA primer will be of sufficient length, as described above, to provide for hybridization to the RCA template under annealing conditions.

In addition to the above nucleic acid components, the reaction mixture for RCA requires a polymerase. For RCA a strand-displacing polymerase should be used e.g. phi29 DNA polymerase. It should not have endonucleolytic activity. Other components required for a DNA polymerase reaction will also be included. The desired polymerase activity may be provided by one or more distinct polymerase enzymes. In some embodiment the polymerase has exonuclease activity, e.g. 5' and/or 3' exonuclease activity.

In preparing the reaction mixture of this step of the subject methods, the various constituent components may be combined in any convenient order. For example, all of the various constituent components may be combined at the same time to produce the reaction mixture.

The amplified products of the RCA reaction (namely the second RCA reaction) may be detected using any convenient protocol, where the particular protocol employed may detect the RCA products non-specifically or specifically, as described in greater detail below. For instance, the second RCA product may be detected directly, e.g. the concatemer may be cleaved to generate monomer which may be detect using gel electrophoresis, or more preferably by hybridizing labelled detection oligonucleotides that hybridize to the reporter domain in the RCA product. Alternatively, the RCA product may be detected indirectly, e.g. the product may be amplified by PCR and the amplification products may be detected.

Representative non-specific detection protocols of interest include protocols that employ signal producing systems that selectively detect single or double stranded DNA products, e.g., via intercalation. Representative detectable molecules that find use in such embodiments include fluorescent nucleic acid stains, such as phenanthridinium dyes, including monomers or homo- or heterodimers thereof, that give an enhanced fluorescence when complexed with nucleic acids. Examples of phenanthridinium dyes include ethidium homodimer, ethidium bromide, propidium iodide, and other alkyl-substituted phenanthridinium dyes. In another embodiment of the invention, the nucleic acid stain is or incorporates an acridine dye, or a homo- or or heterodimer thereof, such as acridine orange, acridine homodimer, ethidium-acridine heterodimer, or 9-amino-6-chloro-2-methoxyacridine. In yet another embodiment of the invention, the nucleic acid stain is an indole or imidazole dye, such as Hoechst 33258, Hoechst 33342, Hoechst 34580 (BIOPROBES 34, Molecular Probes, Inc. Eugene, Oreg., (May 2000)) DAPI (4', 6-diamidino-2-phenylindole) or DIPI (4'6-(diimidazolin-2-yl)-2-phenylindole). Other permitted nucleic acid stains include, but are not limited to, 7-aminoactinomycin D, hydroxystilbamidine, LDS 751, selected psoralens (furocoumarins), styryl dyes, metal complexes such as ruthenium complexes, and transition metal complexes (incorporating $Tb^{3+}$ and $Eu^{3+}$, for example). In certain embodiments of the invention, the nucleic acid stain is a cyanine dye or a homo- or heterodimer of a cyanine dye that gives an enhanced fluorescence when associated with nucleic acids. Any of the dyes described in U.S. Pat.No.4,883,867 to Lee (1989), U.S. Pat. No. 5,582,977 to Yue et al. (1996), U.S. Pat. No. 5,321,130 to Yue et al. (1994), and U.S. Pat. No. 5,410,030 to Yue et al. (1995) (all four patents incorporated by reference) may be used, including nucleic acid stains commercially available under the trademarks TOTO, BOBO, POPO, YOYO, TO-PRO, BO-PRO, PO-PRO and YO-PRO from Molecular Probes, Inc., Eugene, Oreg. Any of the dyes described in U.S. Pat. No. 5,436,134 to Haugland et al. (1995), U.S. Pat. No. 5,658,751 to Yue et al. (1997), and U.S. Pat. No. 5,863,753 to Haugland et al. (1999) (all three patents incorporated by reference) may be used, including nucleic acid stains commercially available under the trademarks SYBR Green, EvaGreen, SYTO, SYTOX, PICOGREEN, OLIGREEN, and RIBOGREEN from Molecular Probes, Inc., Eugene, Oreg. In yet other embodiments of the invention, the nucleic acid stain is a monomeric, homodimeric or heterodimeric cyanine dye that incorporates an aza- or polyazabenzazolium heterocycle, such as an azabenzoxazole, azabenzimidazole, or azabenzothiazole, that gives an enhanced fluorescence when associated with nucleic acids, including nucleic acid stains commercially available under the trademarks SYTO, SYTOX, JOJO, JO-PRO, LOLO, LO-PRO from Molecular Probes, Inc., Eugene, Oreg.

In yet other embodiments, a signal producing system that is specific for the RCA product, as opposed to nucleic acid molecules in general, may be employed to detect the amplification. In these embodiments, the signal producing system may include a probe nucleic acid or oligonucleotide that specifically binds to a sequence found in the RCA product (i.e. a reporter domain sequence), where the probe nucleic acid/oligonucleotide may be labelled with a directly or indirectly detectable label. A directly detectable label is one that can be directly detected without the use of additional reagents, while an indirectly detectable label is one that is detectable by employing one or more additional reagents, e.g., where the label is a member of a signal producing system made up of two or more components. In many embodiments, the label is a directly detectable label, where directly detectable labels of interest include, but are not limited to: fluorescent labels, radioisotopic labels, chemiluminescent labels, and the like. In many embodiments, the label is a fluorescent label, where the labelling reagent employed in such embodiments is a fluorescently tagged nucleotide(s), e.g. fluorescently tagged CTP (such as Cy3-CTP, Cy5-CTP) etc. Fluorescent moieties which may be used to tag nucleotides for producing labelled probe nucleic acids (i.e. detection probes) include, but are not limited to: fluorescein, the cyanine dyes, such as Cy3, Cy5, Alexa 555, Bodipy 630/650, and the like. Other labels, such as those described above, may also be employed as are known in the art.

In certain embodiments, the specifically labelled probe nucleic acids (detection probes) are labelled with "energy transfer" labels. As used herein, "energy transfer" refers to the process by which the fluorescence emission of a fluorescent group is altered by a fluorescence-modifying group. Energy transfer labels are well known in the art, and such labelled oligonucleotide probes include the TaqMan® type probes, as described in U.S. Pat. No. 6,248,526, the disclosure of which is herein incorporated by reference (as well as Held et al., Genome Res. (1996) 6:986-994; Holland et al., Proc. Natl Acad. Sci. USA (1991) 88:7276-7280; and Lee et al., Nuc. Acids Res. (1993) 21:3761-3766). Further examples of detection probes include: Scorpion probes (as described in Whitcombe et al., Nature Biotechnology (1999) 17:804-807; U.S. Pat. No. 6,326,145, the disclosure of which is herein incorporated by reference), Sunrise probes (as described in Nazarenko et al., Nuc. Acids Res. (1997) 25:2516-2521; U.S. Pat. No. 6,117,635, the disclosure of which is herein incorporated by reference), Molecular Beacons (Tyagi et al., Nature Biotechnology (1996) 14:303-308; U.S. Pat. No. 5,989,823, the disclosure of which is incorporated herein by reference), and conformationally assisted probes (as described in provisional application serial no. 60/138,376, the disclosure of which is herein incorporated by reference).

Thus, determining the presence of the second RCA product may be achieved using any convenient protocol. The reaction mixture may be screened etc. (i.e., assayed, assessed, evaluated, tested, etc.) for the presence of any resultant second, and optionally first, RCA products in order to detect the presence of the target analyte in the sample being assayed. The particular detection protocol may vary depending on the sensitivity desired and the application in which the method is being practiced.

The RCA product may be detected in a number of different ways. For example, the nucleotides incorporated in the RCA product may be directly labelled, e.g., fluorescently, or otherwise spectrophotometrically, or radioisotopically labelled or with any signal-giving label, such that the RCA product is directly labelled. In some embodiments detection probes as discussed above, e.g., fluorescently labelled probes, molecular beacons (as described above) etc. may be employed to detect to the presence of the RCA product, where these probes are directed to a sequence (reporter domain sequence, i.e. a sequence that is identical to the reporter domain sequence in the RCA template) that is repeated in the RCA concatemer and therefore only exists in its entirety in the RCA product.

The reaction mixture prepared in this detection step of the subject methods may further include an aqueous buffer medium that includes a source of monovalent ions, a source of divalent cations and a buffering agent. Any convenient source of monovalent ions, such as KCl, K-acetate, $NH_4$-acetate, K-glutamate, $NH_4Cl$, ammonium sulphate, and the like may be employed. The divalent cation may be magnesium, manganese, zinc and the like, where the cation will typically be magnesium. Any convenient source of magnesium cation may be employed, including $MgCl_2$, Mg-acetate, and the like. The amount of $Mg^{2+}$ present in the buffer may range from 0.5 to 10 mM, although higher or lower amounts may be used and may depend on the type of reaction. For instance, for PCR the amount of $Mg^2+$ present in the buffer may be about 1.5 mM, whereas for RCA, the amount of $Mg^2+$ present in the buffer may about 10 mM. Representative buffering agents or salts that may be present in the buffer include Tris, Tricine, HEPES, MOPS and the like, where the amount of buffering agent will typically range from about 5 to 150 mM, usually from about 10 to 100 mM, and more usually from about 20 to 50 mM, where in certain preferred embodiments the buffering agent will be present in an amount sufficient to provide a pH ranging from about 6.0 to 9.5, where most preferred is pH 7.3 at 72° C. Other agents which may be present in the buffer medium include chelating agents, such as EDTA, EGTA and the like.

The next step in the subject methods is signal detection from the labelled RCA products of interest, where signal detection may vary depending on the particular signal producing system employed. In certain embodiments, merely the presence or absence of detectable signal, e.g., fluorescence, is determined and used in the subject assays, e.g., to determine or identify the presence or absence of the second RCA product (and hence the target analyte). Depending on the particular label employed, detection of a signal may indicate the presence or absence of the second RCA product.

In those embodiments where the signal producing system is a fluorescent signal producing system, signal detection typically includes detecting a change in a fluorescent signal from the reaction mixture to obtain an assay result. In other words, any modulation in the fluorescent signal generated by the reaction mixture is assessed. The change may be an increase or decrease in fluorescence, depending on the nature of the label employed, but in certain embodiments is an increase in fluorescence. The sample may be screened for an increase in fluorescence using any convenient means, e.g., a suitable fluorimeter, such as a thermostable-cuvette or plate-reader fluorimeter, or, for example where the sample is a tissue sample on a microscope slide, fluorescence may be detected using a fluorescence microscope. Fluorescence is suitably monitored using a known fluorimeter. The signals from these devices, for instance in the form of photomultiplier voltages, are sent to a data processor board and converted into a spectrum associated with each sample tube. Multiple tubes, for example 96 tubes, can be assessed at the same time. Thus, in some embodiments multiple analytes may be detected in parallel, whereas in other embodiments multiple analytes may be detected sequentially, e.g. one analyte at a time or one group of analytes at a time.

Where the detection protocol is a real time protocol, e.g., as employed in real time PCR reaction protocols, data may be collected in this way at frequent intervals, for example once every 3 minutes, throughout the reaction. By monitoring the fluorescence of the reactive molecule from the sample during each cycle, the progress of the amplification reaction can be monitored in various ways. For example, the data provided by melting peaks can be analyzed, for example by calculating the area under the melting peaks and these data plotted against the number of cycles.

The spectra generated in this way can be resolved, for example, using "fits" of pre-selected fluorescent moieties such as dyes, to form peaks representative of each signalling moiety (i.e. fluorophore). The areas under the peaks can be determined which represents the intensity value for each signal, and if required, expressed as quotients of each other. The differential of signal intensities and/or ratios will allow changes in labelled probes to be recorded through the reaction or at different reaction conditions, such as temperatures. The changes are related to the binding phenomenon between the oligonucleotide probe and the target sequence or degradation of the oligonucleotide probe bound to the target sequence. The integral of the area under the differential peaks will allow intensity values for the label effects to be calculated.

Screening the mixture for a change in fluorescence provides one or more assay results, depending on whether the sample is screened once at the end of the primer extension reaction, or multiple times, e.g., after each cycle, of an amplification reaction (e.g., as is done in real time PCR monitoring).

The data generated as described above can be interpreted in various ways. In its simplest form, an increase or decrease in fluorescence from the sample in the course of or at the end of the amplification reaction is indicative of an increase in the amount of the target analyte present in the sample, e.g. as correlated to the amount of RCA product detected in the reaction mixture, suggestive of the fact that the amplification reaction has proceeded and therefore the target analyte was in fact present in the initial sample. Quantification is also possible by monitoring the amplification reaction throughout the amplification process. Quantification may also include assaying for one or more nucleic acid controls in the reaction mixture, as described above.

In this manner, a reaction mixture may readily be screened (or assessed or assayed etc.) for the presence of RCA product, and hence of target analyte(s), e.g. nucleic acid analytes. The methods are suitable for detection of a single target analyte as well as multiplex analyses, in which two or more different target analytes are assayed in the sample. In these latter multiplex situations, the number of different probes that may be employed for detection may typically range from about 2 to about 20 or higher, e.g., as up to 100 or higher, 1000 or higher, etc. wherein the multiple analytes in a sample may be detected in parallel or sequentially.

The analysis of many analytes simultaneously and in a single reaction using several different probes (multiplexing) may enhanced by the increased sensitivity, and in certain embodiments also increased specificity, which may be obtained using the methods of the invention. Each analyte may be detected via a distinct first RCA template that produces a RCA product that can be used to determine the presence or absence, quantity and/or location of the analytes being assayed. The RCA product may be detected using any of the well-established methods for analysis of nucleic acid molecules known from the literature including liquid chromatography, electrophoresis, mass spectrometry, microscopy, real-time PCR, fluorescent probes, microarray, colorimetric analysis such as ELISA, flow cytometry, mass spectrometry (CyTOF) etc.

As noted above, the methods of the present invention may be employed homogeneously (i.e. in solution) or heterogeneously, using a solid phase. The use of solid phase assays offers advantages, particularly for the detection of difficult samples: washing steps can assist in the removal of unligated molecules etc., inhibiting components, and analytes can be enriched from an undesirably large sample volume.

The manner or means of immobilisation and the solid support may be selected, according to choice, from any number of immobilisation means and solid supports as are widely known in the art and described in the literature. Thus the selected reagent or component for immobilisation may be directly bound to the support (e.g. chemically cross-linked), it may be bound indirectly by means of a linker group, or by an intermediary binding group(s) (e.g. by means of a biotin-streptavidin interaction). Thus, a monomer unit or second RCA primer or product may be provided with means for immobilisation (e.g. an affinity binding partner, e.g. biotin or a hapten or a nucleic acid molecule, capable of binding to its binding partner, i.e. a cognate binding partner, e.g. streptavidin or an antibody or a nucleic acid molecule) provided on the support.

The solid support may be any of the well-known supports or matrices which are currently widely used or proposed for immobilisation, separation etc. These may take the form of particles (e.g. beads which may be magnetic or non-magnetic), sheets, gels, filters, membranes, fibres, capillaries, or microtitre strips, tubes, plates or wells etc.

The support may be made of glass, silica, latex or a polymeric material. Suitable are materials presenting a high surface area for binding of the analyte. Such supports may have an irregular surface and may be for example porous or particulate e.g. particles, fibres, webs, sinters or sieves. Particulate materials e.g. beads are useful due to their greater binding capacity, particularly polymeric beads.

Conveniently, a particulate solid support used according to the invention will comprise spherical beads. The size of the beads is not critical, but they may for example be of the order of diameter of at least 1 and preferably at least 2 µm, and have a maximum diameter of preferably not more than 10, and e.g. not more than 6 µm.

Monodisperse particles, that is those which are substantially uniform in size (e.g. size having a diameter standard deviation of less than 5%) have the advantage that they provide very uniform reproducibility of reaction. Representative monodisperse polymer particles may be produced by the technique described in US-A-4336173.

However, to aid manipulation and separation, magnetic beads are advantageous. The term "magnetic" as used herein means that the support is capable of having a magnetic moment imparted to it when placed in a magnetic field, i.e. paramagnetic, and thus is displaceable under the action of that field. In other words, a support comprising magnetic particles may readily be removed by magnetic aggregation, which provides a quick, simple and efficient way of separating the particles following the analyte binding steps.

In a further embodiment, the analyte itself may be immobilised (or immobilisable) on the solid phase e.g. by non-specific absorption. In a particular such embodiment, the analyte may be present within cells, being optionally fixed and/or permeabilised, which are (capable of being) attached to a solid support, e.g. a tissue sample comprising analyte may be immobilised on a microscope slide.

As noted above the above described methods for detecting the presence of one or more target analytes in a complex sample find use in a variety of different applications.

The subject methods may be used to screen a sample for the presence or absence of one or more target analytes in a sample or for quantifying the amount of one or more target analytes in a sample.

It will be evident from the description above and the representative examples described below that the methods and probes of the invention have advantages over existing methods. Notably, the methods allow for signal amplification of the signal from the first RCA product, thereby increasing the sensitivity of the method, and, as also noted above, faster signal generation. Increased sensitivity may permit analytes to be detected which are present only in low amounts, for example rare events, such as in the detection of pathogens or microorganisms in clinical samples. Thus in a method according to the present invention, a first RCA product may be generated in a highly specific manner, that is production of the first RCA product, or indeed first RCA template, may be strictly dependent upon the presence of an analyte (e.g. in the case of a padlock probe, or an assay using proximity probes which must both bind and interact to generate a circular RCA template). Advantageously, according to the method, the second RCA is dependent upon the presence of the first RCA product, but the requirement for specificity in this second RCA step is less strict (indeed it can be much less strict).

The strong signal amplification afforded by the second RCA reaction may allow ready and easy visualisation of signals, for example microscopically at low magnification or on a digitally scanned image and hence may permit rapid and easy visual inspection of assay results in a clinical scenario, e.g. inspection of pathology results in routine use. Thus the methods of the invention are particularly suited to clinical analysis procedures.

The methods of the invention are described herein with reference to the following Figures.

FIG. 1 depicts the formation of an RCA template from a monomeric unit obtained from a concatenated RCA product comprising monomeric repeats. The RCA template is produced as follows: a first single-stranded concatemeric RCA product is created from a first circular template (1) that has been designed to include at least two copies of a recognition site for a palindromic restriction enzyme (2), so that self-complementary repeats are present in the sequence of the concatenated RCA monomeric repeats (3). The repeated palindromic sequences are able to form an intramolecular stem-like structure, and thus form a double-stranded substrate for a restriction enzyme, which can cleave the probe. The part of the RCA sequence that is present in the loop (4) is removed and the next, shorter, generation of circles (6) is formed via ligation using an external oligonucleotide as a template (5). The external oligonucleotide then also functions to prime RCA.

FIG. 2 depicts the formation of an RCA template from a monomeric unit obtained from a concatenated RCA product comprising monomeric repeats. The RCA template is produced as follows: a first single-stranded concatemeric RCA product is created from a first circular template (1) that has been designed to include two copies of a recognition site for a restriction enzyme (2), so that the recognition sequence for a restriction enzyme is present in the sequence of the concatenated RCA monomeric repeats (3). A sequence complementary to the recognition sequence for the restriction enzyme plus flanking regions may hybridize to the RCA product, forming a double-stranded substrate for a restriction enzyme that may be cleaved using a restriction enzyme in a subsequent or concurrent step (4). Either or both fragments are formed into the next, shorter, generation of circles (5) for amplification, directed by the selection of the oligonucleotide used for ligation (6). The external oligonucleotide then also functions as to prime RCA.

FIG. 3 depicts the formation of an RCA template from a monomeric unit obtained from a concatenated RCA product comprising monomeric repeats. The RCA template is produced as follows: a first single-stranded concatemeric RCA product is created from a first circular template (1) that has been designed to include one or more copies of a recognition site for a restriction enzyme (2), so that the recognition sequence for a restriction enzyme is present in the sequence of the concatenated RCA monomeric repeats (3). A sequence complementary to the recognition sequence for the restriction enzyme plus flanking regions may hybridize to the RCA product, forming a double-stranded substrate for a restriction enzyme that may be cleaved using a restriction enzyme in a subsequent or concurrent step, using a type II subclass of restriction enzyme, wherein digestion is directed outside the recognition sequence of the enzyme itself (4). The next, shorter, generation of circles (5) is formed via ligation using a second external oligonucleotide as a template (6). The external oligonucleotide then also functions as to prime RCA FIG. 4 depicts the formation of an RCA template from a monomeric unit obtained from a concatenated RCA product comprising monomeric repeats. The RCA template is produced as follows: a first single-stranded concatemeric RCA product is created from a first circular template (1) that has been designed to include sequences capable of forming a stem-like structure (2) so that self-complementary repeats are present in the sequence of the concatenated RCA monomeric repeats (3). The stem-like structure can be with or without a loop part (4). The stem part forms a double stranded substrate for a restriction enzyme, which can cleave the probe. The part of the RCA product that is present in the loop (4) is then removed, and the next, shorter, generation of circles (5) is formed via ligation using the circle as a template by itself. An external oligonucleotide functions to prime RCA (6).

EXAMPLES

Example 1

This Example provides a protocol for performing a rolling circle amplification to amplify a circular DNA molecule. Each monomer repeat comprises two restriction enzyme recognition sequences (shown in bold in Table 1) and may be cleaved into two shorter monomer units by a restriction oligonucleotide, as shown in FIG. 2).

TABLE 1

| SEQ ID NO:1 | Sequence circular DNA | CCTTTGCTCATTGACAGA *GTGTATGGAGCTCCTCAGTATAGTCGATAGTAAGCACGGCTA GTGTATGGAGCTCCTCAGTA* CTTTTGGAAGGGAGTA |
|---|---|---|
| SEQ ID NO: 2 | Replication Oligonucleotide | 5'-GTGTATGCAGCTCCTCAGTA-3' |
| SEQ ID NO: 3 | RCA product (monomer shown) | 5'-TACTCCCTTCCAAAAG *TACTGAGGAGCTGCATACAC* TAGCCGTGCTTACTATCGACTA *TACTGAGGAGCTGCATACAC* TCTGTCAATGAGCAAAGG-3' |
| SEQ ID NO: 4 | Monomer 1 | 5'-*CTGCATACAC* TCTGTCAATGAGCAAAGGTACTCCCTTCCAAAAG *TACTGAGGAG*-3' |
| SEQ ID NO: 5 | Monomer 2 | 5'-*CTGCATACAC* TAGCCGTGCTTACTATCGACTA *TACTGAGGAG*-3' |

A first circular RCA template (Sequence circular DNA) is used to generate a first RCA product. A replication oligonucleotide capable of hybridising to the first RCA product binds to the RCA product and templates the formation of a restriction enzyme recognition site (AluI). Two AluI sites are present per monomer repeat (96 nt), and thus each monomer repeat is cut twice, resulting in the formation of two separate, shorter monomer units (monomer 1-54 nt and monomer 2-42 nt).

The monomer units may both be ligated to form two separate, second RCA templates, which are reduced in size compared to the first RCA template. Ligation may be templated by the same oligonucleotide as was used to template the formation of the AluI sites in the previous step. Two separate second RCA reactions may then proceed, which may be primed by the same oligonucleotide. An exemplary protocol for performing each step is provided in Table 2 below.

TABLE 2

|  |  | conc |  | final conc |  | vol | l |
|---|---|---|---|---|---|---|---|
| First RCA reaction |  |  |  |  |  |  |  |
| Circular DNA |  | 10 fM |  | 1 fM |  | 5 | 5 |
| BSA | (Sigma Aldrich) | 10 | µg/µl, stf | 0.2 | µg/µl | 0.80 | 0.8 |
| dNTPs | (Thermo Fisher) | 25 | mM | 156.25 | µM | 0.25 | 0.25 |
| φ29 bfr | (Thermo Fisher) | 10 | x | 1 | x | 4.00 | 4 |
| φ29 pol | (Thermo Fisher) | 10 | U/µl | 50 | mU/µl | 0.20 | 0.2 |
| dH₂O |  |  |  |  |  | 34.75 | 34.75 |
|  |  |  |  | mix volume |  | 40.00 | 40 |
|  |  |  |  | Aliquot volume |  |  | 40.0 |
| Flip tubes and spin down |  |  |  | total volume |  | 40.00 | 40 |
| 37° C. 15 min |  |  |  |  |  |  |  |
| 70° C. 2 min |  |  |  |  |  |  |  |
| 20° C. |  |  |  |  |  |  |  |
| Spin down before opening |  |  |  |  |  |  |  |
| Digestion |  |  |  |  |  |  |  |
| BSA sterile filt. | (Sigma Aldrich) | 10 | µg/µl | 0.2 | µg/µl | 0.20 | 0.2 |
| φ29 bfr | (Thermo Fisher) | 10 | x | 1 | x | 1.00 | 1 |
| AluI | (New England Biolabs) | 10 | U/µl | 0.1 | U/µl | 0.50 | 0.5 |
| Replication oligo (RO) | (Biomers) | 100 | µM | 90 | nM | 0.05 | 0.0 |
| dH₂O |  | — |  | — |  | 8.26 | 8.3 |
|  |  |  |  | mix volume |  | 10.00 | 0 |
|  |  |  |  | Aliquot volume |  |  | 10.0 |
| Vortex tubes and spin down |  |  |  | total volume |  | 50.00 | 50 |
| 37° C. 10 min |  |  |  |  |  |  |  |
| 70° C. 2 min |  |  |  |  |  |  |  |
| 20° C. |  |  |  |  |  |  |  |
| Spin down before opening |  |  |  |  |  |  |  |
| Ligation |  |  |  |  |  |  |  |
| BSA sterile filt. | (Thermo Fisher) | 10 | µg/µl | 0.2 | µg/µl | 0.20 | 0.2 |
| ATP | (Sigma Aldrich) | 100 | mM | 0.12 | mM | 0.06 | 0.06 |
| T4 DNA ligase | (New England Biolabs) | 1 | U/ul | 8.33 | mU/µl | 0.50 | 0.5 |
| dH₂O |  | — |  | — |  | 9.24 | 9.24 |
|  |  |  |  | mix volume |  | 10.00 | 0.0 |
|  |  |  |  | Aliquot volume |  |  | 10.0 |

TABLE 2-continued

|  |  | conc |  | final conc |  | vol | l |
|---|---|---|---|---|---|---|---|
| Vortex tubes and spin down |  |  |  | total volume |  | 60.00 | 60 |
| 37° C. 15 min |  |  |  |  |  |  |  |
| 65° C. 2 min |  |  |  |  |  |  |  |
| 20° C. |  |  |  |  |  |  |  |
| Spin down before opening |  |  |  |  |  |  |  |
| Second RCA reaction |  |  |  |  |  |  |  |
| BSA | (Thermo Fisher) | 10 | µg/µl, stf | 0.2 | µg/µl, stf | 0.40 | 0.4002 |
| dNTPs | (Thermo Fisher) | 25 | mM | 156.25 | µM | 0.44 | 0.4 |
| φ29 bfr | (Thermo Fisher) | 10 | x | 1 | x | 1.00 | 1 |
| φ29 pol | (Thermo Fisher) | 10 | U/µl | 50 | mU/µl | 0.35 | 0.35 |
| dH$_2$O |  |  |  |  |  | 67.81 | 7.81 |
|  |  |  |  | mix volume |  | 10.00 | 0.0 |
|  |  |  |  | Aliquote volume |  |  | 10.0 |
| Vortex tubes and spin down |  |  |  | total volume |  | 70.00 | 70 |
| 37° C. 15 min |  |  |  |  |  |  |  |
| 65° C. 2 min* |  |  |  |  |  |  |  |
| 20° C. |  |  |  |  |  |  |  |
| Spin down before opening |  |  |  |  |  |  |  |

The invention claimed is:

1. A method of detecting and/or analyzing a nucleic acid molecule, said method comprising:
performing a rolling circle amplification (RCA) reaction comprising at least two rounds of RCA, wherein said reaction comprises:
(a) providing a concatemeric first RCA product comprising a multiplicity of monomer repeats, each repeat representing a complementary copy of a first RCA template, wherein said nucleic acid molecule to be detected and/or analyzed, or its complement, is contained in said first RCA template;
(b) cleaving the first RCA product into monomer units, wherein the monomer unit is reduced in size as compared to the monomer repeat of the first RCA product;
(c) circularizing monomer units resulting from said cleavage to form second RCA templates wherein the second RCA template is smaller than the first RCA template; and
(d) performing a second RCA reaction using said second RCA template of (c) and a primer for said second RCA, to form a second RCA product;
wherein any one or more of steps (a) to (d) may be performed sequentially or in combination; and
detecting and/or analyzing said second RCA product and/or a monomer unit derived therefrom.

2. The method of claim 1, wherein steps (b) to (d) are repeated one or more times.

3. The method of claim 1, wherein steps (b) and (c) are performed in combination.

4. The method of claim 1, wherein step (a) comprises the step of generating a first RCA product from a first RCA template.

5. The method of claim 1, wherein cleavage of the first RCA product results directly in the generation of a monomer unit having a reduced size.

6. The method of claim 1, wherein said method comprises a separate step of reducing the size of a monomer unit created by the cleavage of the first RCA product.

7. The method of claim 1, wherein said cleavage is performed using a cleavage enzyme.

8. The method of claim 1, wherein each monomer repeat of the first RCA product comprises one or more cleavage recognition sites.

9. The method of claim 8, wherein a double-stranded cleavage recognition site is provided by intramolecular hybridization of two self-complementary regions of the first RCA product, said intramolecular hybridization creating a stem-like structure, and/or by intermolecular hybridization to a complementary cleavage oligonucleotide.

10. The method of claim 1, wherein each monomer repeat comprises a single cleavage recognition site.

11. The method of claim 1, wherein each monomer repeat contains two or more cleavage recognition sites.

12. The method of claim 1, wherein the cleavage enzyme is a restriction enzyme.

13. The method of claim 1, wherein the monomer units of step (c) are circularized by ligation using a separately provided ligation template oligonucleotide.

14. The method of claim 13, wherein the ligation template oligonucleotide serves as a primer for the second RCA reaction.

15. The method of claim 1, wherein a primer for the second RCA reaction is separately provided.

16. The method of claim 1, wherein the monomer units of step (c) are able to hybridize into an 'open circle' structure capable of self-templated ligation.

17. The method of claim 1, wherein the cleavage recognition site is contained in the stem of a stem-loop structure, and the cleavage releases the loop part of the structure and a residual reduced monomer unit, wherein the loop part is optionally retained as a separate monomer unit.

18. The method of claim 1, wherein each monomer repeat contains two or more cleavage sites and cleavage releases the reduced monomer units from between the cleavage sites.

19. The method of claim 18, wherein the cleavage site is formed by hybridization of a cleavage oligonucleotide, and optionally the same oligonucleotide is used as ligation template for circularization of the monomer units.

20. The method of claim 1, wherein each monomer repeat contains a single cleavage recognition site for a type IIs restriction enzyme, wherein cleavage occurs externally to the cleavage recognition site.

21. The method of claim 1, wherein each monomer repeat comprises two or more deoxyribozyme sequences, wherein upon activation the deoxyribozymes act to cleave the first RCA product.

22. The method of claim 1, wherein each monomer repeat of the first RCA product comprises one or more stem-like structures comprising a nicking site for cleavage by a nickase enzyme to release monomer units.

23. The method of claim 1, wherein each monomer repeat of the first RCA product comprises one or more stem-like structures comprising a restriction site for cleavage by a restriction enzyme to release monomer units, wherein the monomer units are able to form self-hybridized open-circle structures capable of self-templated ligation to form second RCA templates.

24. The method of claim 23, wherein each monomer repeat comprises two or more stem-like structures and/or wherein a loop part of the stem-like structure is removed.

25. The method of claim 1, wherein a monomer unit released by cleavage of the first RCA product is hybridized to a ligation template to create a structure having a protruding end which is removed by cleavage to form a reduced monomer unit.

26. The method of claim 1, wherein cleavage of the first RCA product results in the generation of different monomer units and it is selected which monomer units are circularized, and optionally wherein said selection is by using ligation templates which hybridize selectively to a selected monomer unit.

27. The method of claim 1, wherein all monomer units are circularized.

28. The method of claim 1, wherein the monomer unit which is circularized comprises a reporter domain.

29. The method of claim 1, wherein the monomer unit which is circularized comprises a target nucleic acid molecule for detection and/or analysis.

30. The method of claim 1, wherein the first RCA template is a reporter molecule, a circularized probe, or a circularized molecule comprising captured target nucleic acid molecule.

31. The method of claim 1, wherein one or more steps of the method are carried out using a solid phase.

32. The method of claim 1, wherein the analysis is sequencing.

33. The method of claim 1, wherein the nucleic acid molecule is a target analyte for detection, or is indicative of the presence of a target analyte in a sample, and wherein the first circular RCA template comprises or is generated from a nucleic acid analyte or is used or generated as a marker for said analyte, and a first RCA reaction is performed using said first RCA template to generate a first RCA product, wherein the target analyte is detected by detecting and/or analyzing said second RCA product and/or a monomer unit derived therefrom.

34. The method of claim 1, wherein said first circular RCA template includes a tag sequence or captured sequence, wherein the complement thereof is retained in the reduced monomer unit and which, or its complement, is detected in the second or subsequent RCA product and/or monomer unit derived therefrom.

* * * * *

SEQUENCE LISTING

<160> NUMBER OF SEQ ID NOS: 5

<210> SEQ ID NO 1
<211> LENGTH: 96
<212> TYPE: DNA
<213> ORGANISM: Artificial Sequence
<220> FEATURE:
<223> OTHER INFORMATION: Sequence circular DNA

<400> SEQUENCE: 1
cctttgctca ttgacagagt gtatgcagct cctcagtata gtcgatagta agcacggcta    60
gtgtatgcag ctcctcagta cttttggaag ggagta    96

<210> SEQ ID NO 2
<211> LENGTH: 20
<212> TYPE: DNA
<213> ORGANISM: Artificial Sequence
<220> FEATURE:
<223> OTHER INFORMATION: Replication oligonucleotide

<400> SEQUENCE: 2
gtgtatgcag ctcctcagta    20

<210> SEQ ID NO 3
<211> LENGTH: 96
<212> TYPE: DNA
<213> ORGANISM: Artificial Sequence
<220> FEATURE:
<223> OTHER INFORMATION: RCA product monomer repeat

<400> SEQUENCE: 3
tactcccttc caaaagtact gaggagctgc atacactagc cgtgcttact atcgactata    60
ctgaggagct gcatacactc tgtcaatgag caaagg    96

<210> SEQ ID NO 4
<211> LENGTH: 54
<212> TYPE: DNA
<213> ORGANISM: Artificial Sequence
<220> FEATURE:
<223> OTHER INFORMATION: Monomer unit 1

```
<400> SEQUENCE: 4
ctgcatacac tctgtcaatg agcaaaggta ctcccttcca aaagtactga ggag              54

<210> SEQ ID NO 5
<211> LENGTH: 42
<212> TYPE: DNA
<213> ORGANISM: Artificial Sequence
<220> FEATURE:
<223> OTHER INFORMATION: Monomer unit 2

<400> SEQUENCE: 5
ctgcatacac tagccgtgct tactatcgac tatactgagg ag                          42
```